(12) United States Patent
Coleman et al.

(10) Patent No.: US 12,144,986 B2
(45) Date of Patent: Nov. 19, 2024

(54) SYSTEMS AND METHODS FOR TREATING OR SUPPORTING HUMAN JOINTS OR A PORTION OF THE HUMAN BODY

(71) Applicant: CyMedica Orthopedics, Inc., Scottsdale, AZ (US)

(72) Inventors: Struan Coleman, Locust Valley, NY (US); Calvin Domenico, Somerville, MA (US); Edison Gieswein, San Antonio, TX (US)

(73) Assignee: MOTIVE HEALTH, INC., Scottsdale, AZ (US)

( * ) Notice: Subject to any disclaimer, the term of this patent is extended or adjusted under 35 U.S.C. 154(b) by 191 days.

(21) Appl. No.: 17/226,948

(22) Filed: Apr. 9, 2021

(65) Prior Publication Data

US 2021/0220643 A1 Jul. 22, 2021

Related U.S. Application Data

(63) Continuation of application No. 14/793,423, filed on Jul. 7, 2015, now abandoned, which is a continuation
(Continued)

(51) Int. Cl.
*A61N 1/36* (2006.01)
*A61F 5/01* (2006.01)
*A61N 1/04* (2006.01)

(52) U.S. Cl.
CPC ........ *A61N 1/36003* (2013.01); *A61F 5/0123* (2013.01); *A61F 5/0125* (2013.01);
(Continued)

(58) Field of Classification Search
CPC ............ A61N 1/36003; A61N 1/36031; A61N 1/36034; A61N 1/0452; A61F 5/0123; A61F 5/0125
See application file for complete search history.

(56) References Cited

U.S. PATENT DOCUMENTS

| 4,326,534 A | 4/1982 | Axelgmrd et al. |
| 4,765,318 A | 8/1988 | Tranberg et al. |

(Continued)

FOREIGN PATENT DOCUMENTS

| CN | 1272798 A | 11/2000 |
| CN | 101041101 A | 9/2007 |

(Continued)

OTHER PUBLICATIONS

China National Intellectual Property Administration; Notification of the First Office Action, issued in connection to CN 201910691121. 8; Oct. 28, 2022.

(Continued)

*Primary Examiner* — Amanda K Hulbert
*Assistant Examiner* — Philip C Edwards
(74) *Attorney, Agent, or Firm* — Greenberg Traurig, LLP

(57) ABSTRACT

Disclosed is a system including a good comprising a sensor in contact with human tissues of a patient and configured to obtain a power dissipation reading of the human tissues. The good also includes a storage medium for tangibly storing thereon a program for execution by a processor. The system also includes a control unit in communication with the good to form an electrical muscular stimulation (EMS) system that uses feedback in a closed loop manner to self tune electrical properties of the output. The control unit is configured to instruct the sensor to (a) apply a sense pulse to the human tissues, (b) measure power dissipation of the sense pulse, (c) adjust a stimulation pulse based on the measured power dissipation, (d) apply the stimulation pulse to the human tissues based on the power dissipation and based on the program in order to maintain constant power output across each pulse, and (e) repeat steps (a)-(d).

8 Claims, 17 Drawing Sheets

Related U.S. Application Data of application No. 14/214,394, filed on Mar. 14, 2014, now Pat. No. 9,072,898, which is a continuation of application No. 14/021,387, filed on Sep. 9, 2013, now Pat. No. 8,870,798.

(60) Provisional application No. 61/784,927, filed on Mar. 14, 2013.

(52) U.S. Cl.
CPC ....... *A61N 1/0484* (2013.01); *A61N 1/36031* (2017.08); *A61N 1/36034* (2017.08); *A61N 1/0452* (2013.01); *A61N 1/0476* (2013.01); *A61N 1/0492* (2013.01)

(56) References Cited

U.S. PATENT DOCUMENTS

| | | |
|---|---|---|
| 4,796,631 A | 1/1989 | Grigoryev |
| 4,832,033 A | 5/1989 | Maher et al. |
| 5,052,375 A | 1/1991 | Stark et al. |
| 5,024,650 A | 6/1991 | Hagiwara et al. |
| 5,368,546 A | 11/1994 | Stark et al. |
| 5,399,147 A | 3/1995 | Kaiser |
| 5,484,389 A | 1/1996 | Stark et al. |
| 5,507,788 A | 4/1996 | Lieber |
| 5,628,722 A | 5/1997 | Solomonow et al. |
| 5,688,584 A | 11/1997 | Casson et al. |
| 5,766,236 A | 6/1998 | Detty et al. |
| 5,947,913 A | 9/1999 | Palumbo |
| 5,980,435 A | 11/1999 | Joutras et al. |
| 6,321,119 B1 | 11/2001 | Kronberg |
| 6,324,432 B1 | 11/2001 | Rigaux et al. |
| 6,341,237 B1 | 1/2002 | Hurtado |
| 6,350,276 B1 | 2/2002 | Knowlton |
| 6,456,885 B1 | 9/2002 | Shiba et al. |
| 6,507,757 B1 | 1/2003 | Swain et al. |
| 6,876,883 B2 | 4/2005 | Hurtado |
| 6,944,503 B2 | 9/2005 | Crow et al. |
| 6,969,365 B2 | 11/2005 | Scorvo |
| 7,135,005 B2 | 11/2006 | Kania |
| 7,198,610 B2 | 4/2007 | Ingimundarson et al. |
| 7,207,963 B2 | 4/2007 | Kania et al. |
| 7,212,854 B2 | 5/2007 | Kovak et al. |
| 7,341,586 B2 | 3/2008 | Daniel et al. |
| 7,367,935 B2 | 5/2008 | Mechlenburg et al. |
| 7,369,895 B2 | 5/2008 | Hurtado |
| 7,713,225 B2 | 5/2010 | Ingimundarson et al. |
| 7,758,527 B2 | 7/2010 | Gilmour et al. |
| 7,794,418 B2 | 9/2010 | Ingimundarson et al. |
| 7,881,780 B2 | 2/2011 | Flaherty |
| 7,991,461 B2 | 8/2011 | Flaherty et al. |
| 8,016,781 B2 | 9/2011 | Ingimundarson et al. |
| 8,025,632 B2 | 9/2011 | Einarsson |
| 8,070,703 B2 | 12/2011 | Skahan et al. |
| 8,209,030 B2 | 6/2012 | Minogue et al. |
| 8,241,234 B2 | 8/2012 | Ingimundarson et al. |
| 8,257,293 B2 | 9/2012 | Ingimundarson et al. |
| 8,265,763 B2 | 9/2012 | Fahey |
| 8,285,381 B2 | 10/2012 | Fahey |
| 8,311,645 B2 | 11/2012 | Bolea et al. |
| 8,328,746 B2 | 12/2012 | Ingimundarson et al. |
| 8,346,367 B2 | 1/2013 | Carroll |
| 8,355,790 B2 | 1/2013 | Naroditsky et al. |
| 8,433,403 B2 | 4/2013 | Fahey |
| 8,454,543 B2 | 6/2013 | Skahan et al. |
| 8,494,625 B2 | 7/2013 | Hargrove |
| 8,560,077 B2 | 10/2013 | Feinstein |
| 8,588,901 B2 | 11/2013 | Fahey |
| 8,870,798 B2 | 10/2014 | Coleman et al. |
| 9,072,898 B2 | 7/2015 | Coleman et al. |
| 2002/0068887 A1 | 6/2002 | Kikumoto et al. |
| 2003/0195586 A1 | 10/2003 | Rigaux et al. |
| 2003/0236487 A1 | 12/2003 | Knowlton |
| 2004/0039426 A1 | 2/2004 | Hurtado |
| 2004/0054379 A1 | 3/2004 | Carroll et al. |
| 2004/0059234 A1 | 3/2004 | Martin et al. |
| 2004/0102723 A1 | 5/2004 | Horst |
| 2004/0210214 A1 | 10/2004 | Knowlton |
| 2004/0254624 A1 | 12/2004 | Johnson |
| 2005/0010265 A1 | 1/2005 | Baru et al. |
| 2005/0131488 A1 | 6/2005 | Hurtado |
| 2005/0215899 A1 | 9/2005 | Trahey et al. |
| 2006/0189899 A1 | 8/2006 | Flaherty et al. |
| 2007/0010772 A1 | 1/2007 | Ryan |
| 2007/0038252 A1 | 2/2007 | Carroll |
| 2007/0129776 A1 | 6/2007 | Robins et al. |
| 2007/0179412 A1 | 8/2007 | Imboden |
| 2007/0179413 A1 | 8/2007 | Imboden et al. |
| 2007/0179414 A1 | 8/2007 | Imboden et al. |
| 2008/0097530 A1 | 4/2008 | Muccio et al. |
| 2008/0228119 A1 | 9/2008 | Ingimundarson et al. |
| 2009/0024062 A1 | 1/2009 | Einarsson |
| 2009/0024065 A1 | 1/2009 | Einarsson |
| 2009/0105558 A1 | 4/2009 | Riley-Doucet et al. |
| 2009/0105795 A1 | 4/2009 | Minogue et al. |
| 2009/0124948 A1 | 5/2009 | Ingimundarson et al. |
| 2009/0182393 A1 | 7/2009 | Bachinski |
| 2009/0182394 A1 | 7/2009 | Bachinski |
| 2009/0248110 A1* | 10/2009 | Choi ................. A61N 1/36038 607/45 |
| 2010/0081979 A1 | 4/2010 | Ingimundarson et al. |
| 2010/0082079 A1 | 4/2010 | Skahan et al. |
| 2010/0174221 A1 | 7/2010 | Ingimundarson et al. |
| 2010/0217349 A1 | 8/2010 | Fahey |
| 2010/0262052 A1 | 10/2010 | Lunau et al. |
| 2011/0009927 A1 | 1/2011 | Parker et al. |
| 2011/0015696 A1 | 1/2011 | Kirm |
| 2011/0066209 A1* | 3/2011 | Bodlaender ........ A61N 1/36021 607/46 |
| 2011/0112605 A1 | 5/2011 | Fahey |
| 2011/0137381 A1 | 6/2011 | Lee et al. |
| 2011/0184326 A1 | 7/2011 | Ingimundarson et al. |
| 2011/0288611 A1 | 11/2011 | Lunau et al. |
| 2011/0295339 A1* | 12/2011 | Carroll ............... A61N 1/36003 607/49 |
| 2012/0030277 A1 | 2/2012 | Pawlowski et al. |
| 2012/0123568 A1 | 5/2012 | Pollard et al. |
| 2012/0136278 A1 | 5/2012 | Gupta et al. |
| 2012/0158456 A1 | 6/2012 | Wang et al. |
| 2012/0197343 A1 | 8/2012 | Lane et al. |
| 2012/0203305 A1 | 8/2012 | Schauer et al. |
| 2012/0259383 A1* | 10/2012 | Trier ................. A61N 1/36146 607/46 |
| 2012/0289763 A1 | 11/2012 | Boyden et al. |
| 2012/0302821 A1 | 11/2012 | Burnett |
| 2012/0303076 A1 | 11/2012 | Fahey |
| 2013/0030277 A1 | 1/2013 | Fahey |
| 2013/0123568 A1 | 5/2013 | Hamilton et al. |
| 2013/0158456 A1 | 6/2013 | Skahan et al. |
| 2013/0246036 A1 | 9/2013 | Kim |
| 2014/0194781 A1 | 7/2014 | Einarsson |
| 2016/0220849 A1 | 8/2016 | Knowlton |

FOREIGN PATENT DOCUMENTS

| | | |
|---|---|---|
| CN | 101678205 A | 3/2010 |
| CN | 102470240 | 5/2012 |
| CN | 202223758 | 5/2012 |
| CN | 105263408 | 1/2016 |
| EP | 2967442 | 1/2016 |
| JP | 2009-538654 | 11/2009 |
| JP | 2012-532672 | 12/2012 |
| JP | 2016-515887 | 6/2016 |
| KR | 10-2005-0071489 A | 7/2005 |
| KR | 10-2008-0059551 A | 6/2008 |
| KR | 10-1064327 B1 | 9/2011 |
| KR | 10-2012-0028928 A | 3/2012 |
| KR | 10-2013-0091653 A | 8/2013 |
| WO | 2004/078255 | 10/2004 |
| WO | 2011/150502 | 12/2011 |
| WO | 2012154633 A1 | 11/2012 |

(56) References Cited

FOREIGN PATENT DOCUMENTS

| WO | 2012142624 A1 | 9/2013 |
|---|---|---|
| WO | 2014/153017 | 9/2015 |
| WO | 2014/153033 | 9/2015 |

OTHER PUBLICATIONS

Kneehag XP®—Quadriceps Strengthening and Pain Management—Advanced Therapy for Quadriceps Muscle Strengthening and Pain Management; http://www.neurotechgroup.com/us/products/kneehab-xp; Retrieved Dec. 17, 2013.

Neurotech®—Kneehab XP® Quadriceps Therapy System—On the Move: clinical News & Insights; Issue 1, Sep. 2010.

U.S. Patent and Trademark Office; PCT International Search Report, Issued in connection to PCT/US14/28698; Aug. 20, 2014; 2 pages; US.

U.S. Patent and Trademark Office; PCT Written Opinion of the International Searching Authority, Issued in connection to PCT/US14/28698; Aug. 20, 2014; 6 pages; US.

The International Bureau of WIPO; PCT International Preliminary Report on Patentabilily, issued in :: onnection to PCT/US2014/028779; Sep. 15, 2015; 6 pages; Switzerland.

U.S. Patent and Trademark Office; PCT International Search Report, issued in connection to PCT/US14/28779; Jan. 30, 2015; 3 pages; U.S.

U.S. Patent and Trademark Office; PCT Written Opinion of the International Searching Authority, issued in :: onnection to PCT/US14/28779; Jan. 30, 2015; 5 pages; U.S.

I\ustralian Government, IP Australia; Examination Report No. 1 for Standard Patent Application, issued in :: onnection to AU2014236364; Sep. 13, 2017; 4 pages; Australia.

State Intellectual Property Office of the People's Republic of China; Notification of the Second ::Iffice Action, Issued in connection to CN201480013922.4; Mar. 29, 2018; 20 pages; China.

State Intellectual Property Office of the People's Republic of China; Notification of the First :: Iffice Action, Issued in connection to CN201480013922.4; Jun. 28, 2017; 18 pages; China.

European Patent Office; Extended European Search Report, Issued in Connection to EP14769785.8; Nov. 11, 2016; 9 pages; Europ.

Japanese Patent Office; Notification of Grounds for Rejection, Issued in connection to JP2016-502871; Mar. 12, 2018; 4 pages; Japan.

Canadian Intellectual Property Office; Office Action, Issued in connection to CA2,904,653; May 7, 2020; 6 pages; Canada.

\* cited by examiner

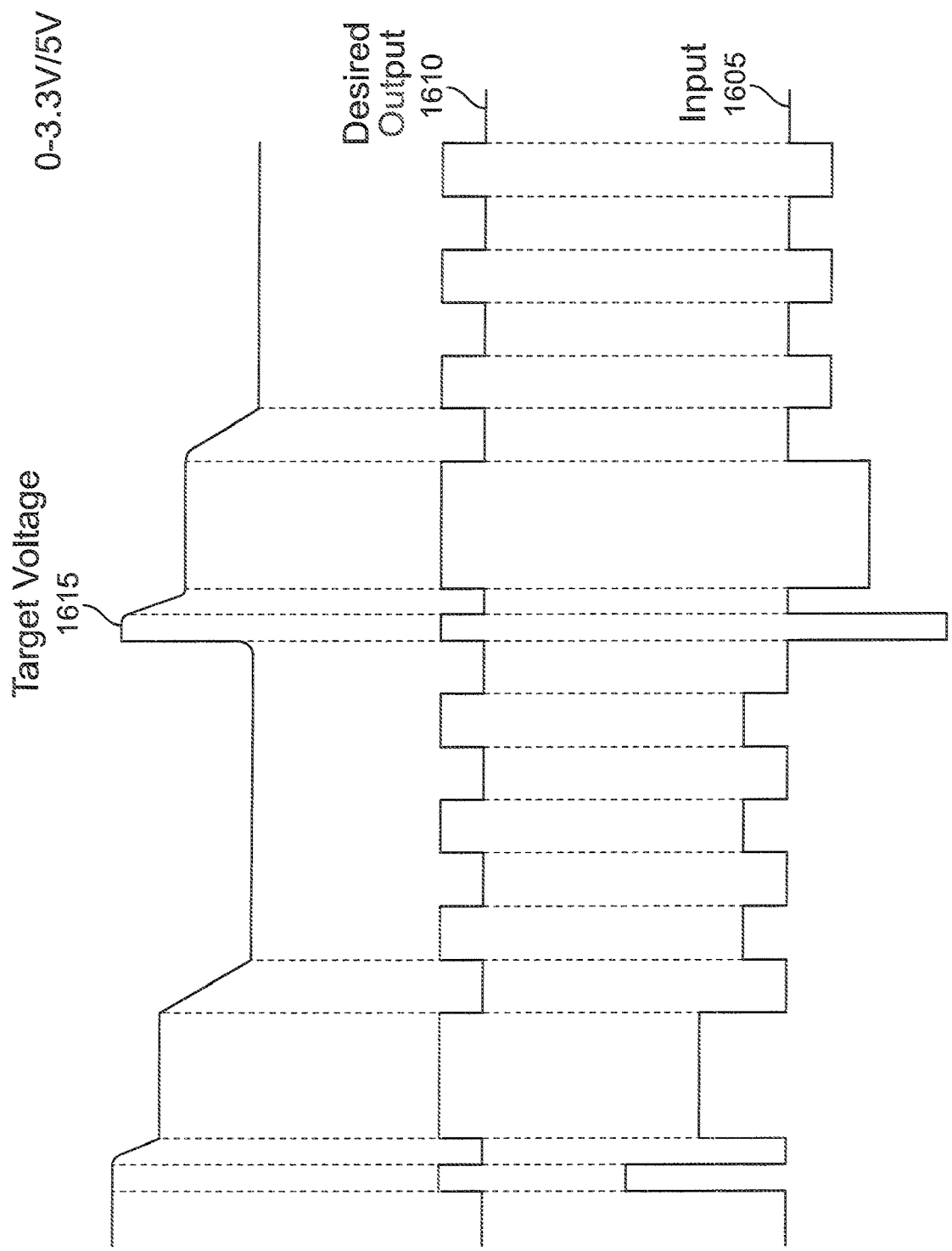

SYSTEMS AND METHODS FOR TREATING OR SUPPORTING HUMAN JOINTS OR A PORTION OF THE HUMAN BODY

CROSS REFERENCE TO RELATED APPLICATIONS

This patent application is a continuation of U.S. patent application Ser. No. 14/793,423, entitled "System and Methods for Treating or Supporting Human Joints or a Portion of the Human Body," filed on Jul. 7, 2015, which is a continuation of U.S. patent application Ser. No. 14/214,394, entitled "System and Methods for Treating or Supporting Human Joints or a Portion of the Human Body," filed on Mar. 14, 2014, which is a continuation of U.S. patent application Ser. No. 14/021,387, entitled "Systems and Methods for Treating Human Joints" filed on Sep. 9, 2013, which claims priority to Provisional Patent Application No. 61/784,927, entitled "Systems and Methods for Treating Human Joints" filed on Mar. 14, 2013, the contents of which are incorporated herein by reference.

FIELD OF THE INVENTION

The present disclosure relates to systems and methods for treating or supporting human joints or a portion of the human body, and more specifically to systems and methods for treating or supporting human joints or a portion of the human body with a combination of support and electrical muscle stimulation with a closed loop feedback system.

BACKGROUND OF THE INVENTION

Orthopedic braces are useful as preventative aids to prevent injuries to joints caused by motions or orientations of the joint that are outside the biomechanical limits of the joint. Orthopedic braces are also useful to promote proper healing of a joint following an injury to, or surgery on, the joint. Braces are also useful as a method to stabilize joints with arthritis, thereby alleviating pain.

Patients usually see a physical therapist to strengthen their muscle(s) after suffering an injury, undergoing surgery, or when afflicted with arthritis, conditions which can result in muscle atrophy. The patient may receive electrical muscle stimulation (EMS) at the start of the physical therapy to loosen their muscles before the exercises and stretching begins. EMS is also used by the therapist (as prescribed by the health care provider) to strengthen muscles that have atrophied. However, the delivery of EMS for muscle strengthening is sub-optimal, as it can only be performed when the patient is with the therapist. Also, current therapy implementations are painful for the patient.

Thus, there remains a need for stimulation that is better suited to allow the patient to treat himself or herself on a more regular basis than just when they are going to physical therapy.

SUMMARY OF THE INVENTION

In one aspect, a system and method include a good comprising an electrode comprising a sensor in contact with human tissues (e.g., skin) of a patient and configured to obtain a measure of power dissipation of the human tissues (e.g., one or more of muscle(s), skin, tissue, fatty layers, etc.) of the patient. The good also includes a storage medium for tangibly storing thereon a program for execution by a processor. Although the good is described herein as a soft good (e.g., a flexible knee brace), the good can alternatively be a hard good (e.g., a rigid cast).

The system and method also include a control unit in communication with the soft good to form an electrical muscle stimulation (EMS) system that uses feedback in a closed loop manner to self tune the electrical properties of the output. The control unit is configured to instruct the sensor to (a) apply a sense pulse to the human tissues, (b) measure power dissipation of the sense pulse, (c) adjust a stimulation pulse based on the measured power dissipation, (d) apply the stimulation pulse to the human tissues based on the power dissipation and based on the program in order to maintain constant power output across each pulse, and (e) repeat steps (a)-(d).

The sense pulse that is produced during an EMS cycle creates a low resistance pathway that allows it to use the minimum required power to produce meaningful results. This means that the electrical muscle stimulation produced by the device is less painful to the user.

Power dissipation is calculated by measuring the difference between source power (e.g., in watts, determined by simultaneously measuring voltage and current) and return power (e.g., in watts, determined by simultaneously measuring voltage and current).

In one embodiment, a knee brace is provided comprising a rigid frame having an upper portion and a lower portion connected by a hinge. The plurality electrodes may be disposed on the upper and/or lower portions of the brace. In another embodiment, a knee brace is provided comprising a flexible sleeve configured to fit over the knee of the patient. The flexible sleeve may, for example, comprise a sheet of fabric, rubber, or other material, adapted to be wrapped around the knee and secured as a sleeve thereon by a fastening means, such as a zipper, buttons, snaps, Velcro (e.g., hook and loop fasteners) and the like. The plurality of electrodes may be disposed on the flexible sleeve. In some embodiments, the electrodes may be disposed on both the hard good (e.g., rigid frame) and soft good (e.g., flexible sleeve). In all embodiments, the electrodes may be permanently affixed the good or may be removably affixed to the good, such that they may be readily removed and repositioned on the good. In one embodiment, the electrodes will include a backing comprising one component of a hook and loop fastener wherein the good may comprise the other component of a hook and loop fastener, such that the electrodes may be reversibly affixed onto the good.

In one embodiment, the soft good provides support to the patient. The soft good can be, for example, a brace, a sleeve, a sling, a garment, a wrap, a cast, and/or a strap. The control unit can instruct the sensor to apply consistent pulses onto the human tissues while the patient is moving, which is possible due to the feedback from the sensor to the control unit of the power dissipation of the user's human tissues. In one embodiment, the storage medium includes a digital identifier identifying what the soft good is. This identifier may be, for example, a numeric code representing the type of soft good. The program selected for execution may be based on the identifier. The program can include specific waveform treatment protocols for each type of soft good. In one embodiment, the control unit executes a program contained in storage on the soft good.

The soft good can be a short brace including a sleeve that is part of the short brace. The soft good can alternatively be a long brace including a removable sleeve that is connected to the long brace via hinges.

In one embodiment, the sensor includes a moisturizer or gel. The sensor may communicate the dryness of the patient's skin to the control unit.

In one embodiment, if the measuring of the power dissipation exceeds preset boundaries, the sensor will not apply the corresponding stimulation pulse. Each sense pulse creates or maintains a conductive channel through the human tissues by exceeding a breakdown voltage of the human tissues.

The system can also include a dedicated voltage controlled power supply present per stimulation channel, thereby eliminating time division of the power output of the generation of the stimulation signal. Two or more simultaneous stimulation pulses of different voltages are possible within the same time domain.

The system can also include optically coupled FETs to generate the stimulation pulse with a minimum EM/RF generation, thereby enabling the system to be used near sensitive medical equipment. In one embodiment, the unit can be deployed directly in a surgical environment. One embodiment of the device may contain multiple EM/RF shields to prevent radiative coupling with other electronic devices.

In one aspect, a control unit for controlling a brace for treating a human joint or body part of a patient includes a processor and a storage medium for tangibly storing thereon an electro-stimulation control program and for tangibly storing thereon program logic for execution by the processor. The program logic includes receiving logic executed by the processor for receiving, from a sensor in contact with skin of the patient, a power dissipation reading of the human tissues, and communication logic executed by the processor for communicating with the sensor to form an electrical muscular stimulation (EMS) system that uses feedback to be self tuning, the communication logic configured to instruct the sensor to (a) apply a sense pulse to the human tissues, (b) measure power dissipation of the sense pulse, (c) adjust a stimulation pulse based on the measured power dissipation, (d) apply the stimulation pulse to the human tissues based on the power dissipation and based on the program in order to maintain constant power output across each pulse, and (e) repeat steps (a)-(d).

In one embodiment, the communication logic includes brace communication logic executed by the processor for communicating with the brace, where the brace provides support to the patient and is a brace, a sleeve, a sling, a garment, a wrap, and/or a strap. The receiving logic may include identifier receiving logic executed by the processor for receiving, from the control program, an identifier that identifies the brace.

These and other aspects and embodiments will be apparent to those of ordinary skill in the art by reference to the following detailed description and the accompanying drawings.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 16 is a waveform diagram of an input waveform, a desired output waveform, and a target voltage in accordance with an embodiment of the disclosure.

DETAILED DESCRIPTION OF THE INVENTION

Figure 1A:
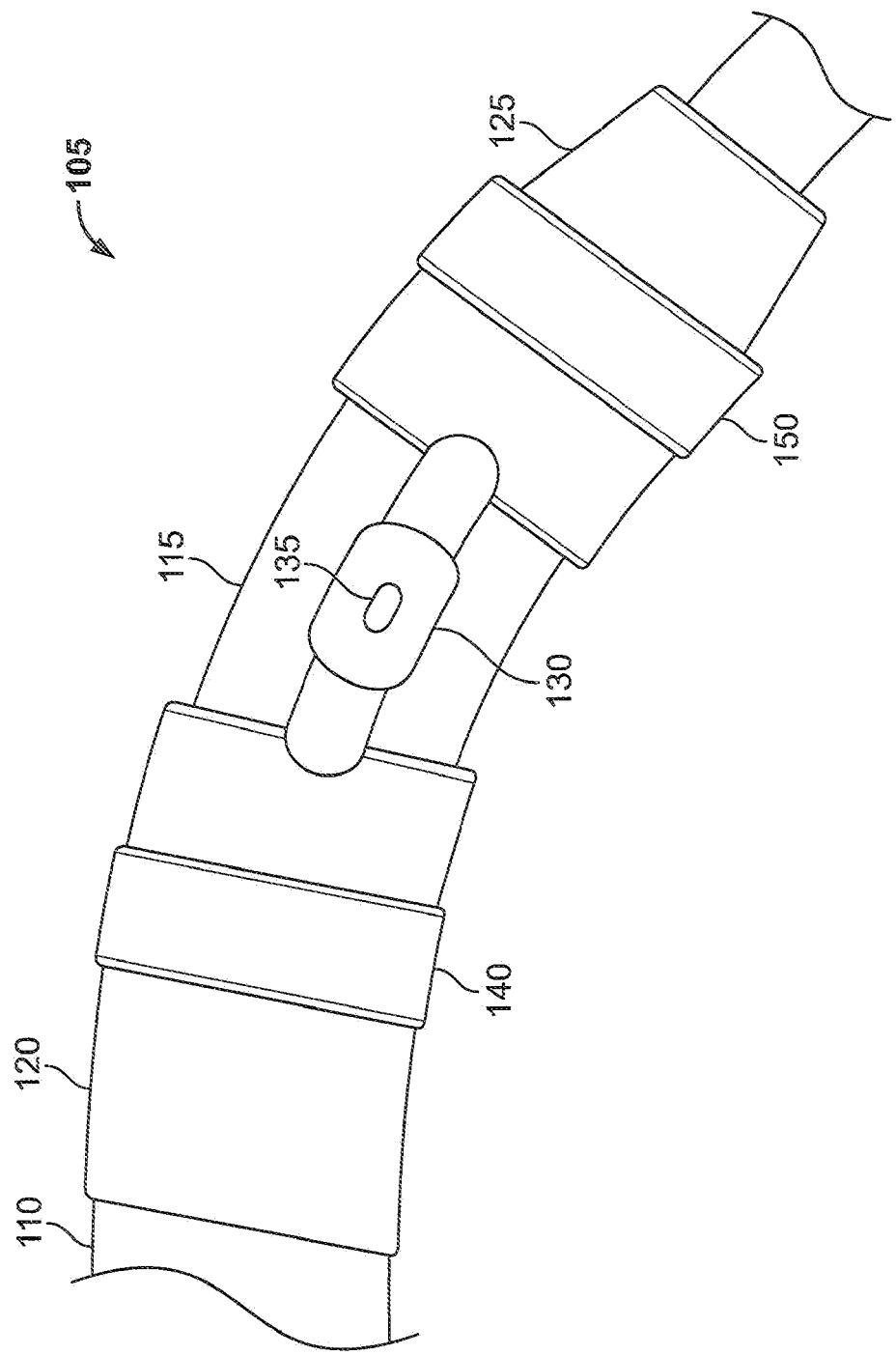
FIG. 1A is a fragmentary perspective view of a knee brace mounted onto the knee of a patient in accordance with an embodiment of the disclosure.

Embodiments are now discussed in more detail referring to the drawings that accompany the present application. In the accompanying drawings, like and/or corresponding elements are referred to by like reference numbers.

Various embodiments are disclosed herein; however, it is to be understood that the disclosed embodiments are merely illustrative of the disclosure that can be embodied in various forms. In addition, each of the examples given in connection with the various embodiments is intended to be illustrative, and not restrictive. Further, the figures are not necessarily to scale, some features may be exaggerated to show details of particular components (and any size, material and similar details shown in the figures are intended to be illustrative and not restrictive). Therefore, specific structural and functional details disclosed herein are not to be interpreted as limiting, but merely as a representative basis for teaching one skilled in the art to variously employ the disclosed embodiments.

Subject matter will now be described more fully hereinafter with reference to the accompanying drawings, which form a part hereof, and which show, by way of illustration, specific example embodiments. Subject matter may, however, be embodied in a variety of different forms and, therefore, covered or claimed subject matter is intended to be construed as not being limited to any example embodiments set forth herein; example embodiments are provided merely to be illustrative. Among other things, for example, subject matter may be embodied as methods, devices, components, or systems. Accordingly, embodiments may, for example, take the form of hardware (e.g., electronics hardware and/or physical mechanical hardware), software, firmware or any combination thereof (other than software per se). The following detailed description is, therefore, not intended to be taken in a limiting sense.

The present disclosure is described below with reference to block diagrams and operational illustrations of methods and devices. It is understood that each block of the block diagrams or operational illustrations, and combinations of blocks in the block diagrams or operational illustrations, can be implemented by means of analog or digital hardware and computer program instructions. These computer program instructions can be provided to a processor of a general purpose computer, special purpose computer, ASIC, FPGA, or other programmable data processing apparatus, such that the instructions, which execute via the processor of the computer or other programmable data processing apparatus, implements the functions/acts specified in the block diagrams or operational block or blocks.

In some alternate implementations, the functions/acts noted in the blocks can occur out of the order noted in the operational illustrations. For example, two blocks shown in succession can in fact be executed substantially concurrently or the blocks can sometimes be executed in the reverse order, depending upon the functionality/acts involved. Furthermore, the embodiments of methods presented and described as flowcharts in this disclosure are provided by way of example in order to provide a more complete understanding of the technology. The disclosed methods are not limited to the operations and logical flow presented herein. Alternative embodiments are contemplated in which the order of the various operations is altered and in which sub-operations described as being part of a larger operation are performed independently.

Throughout the specification and claims, terms may have nuanced meanings suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter include combinations of example embodiments in whole or in part.

In general, terminology may be understood at least in part from usage in context. For example, terms, such as "and", "or", or "and/or," as used herein may include a variety of meanings that may depend at least in part upon the context in which such terms are used. Typically, "or" if used to associate a list, such as A, B, or C, is intended to mean A, B, and C, here used in the inclusive sense, as well as A, B, or C, here used in the exclusive sense. In addition, the term "one or more" as used herein, depending at least in part upon context, may be used to describe any feature, structure, or characteristic in a singular sense or may be used to describe combinations of features, structures or characteristics in a plural sense. Similarly, terms, such as "a," "an," or "the," again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

Although described below as a brace associated with a patient's knee, the brace described herein may be used to brace any human joint, such as the hip, shoulder, ankle, elbow, wrist, spine, and/or back. Further, the brace may be used to treat or prescribed/recommended to treat a joint after surgery, for arthritis, after injury, etc.

As described in more detail below, the human knee generally comprises an articulated joint between the thigh and the calf muscles that supports the weight of the human body while the person is standing, walking or running. The knee joint is primarily held together by four ligaments; namely, the anterior cruciate ligament (ACL), the posterior cruciate ligament (PCL), the medial collateral ligament (MCL), and the lateral collateral ligament (LCL). The knee joint can be weakened or damaged by injuries resulting in cartilage damage and ligament strain, which may be the result of trauma, repetitive sporting activities or overly aggressive exercising, or physiological problems such as occurs with the arthritidies. In particular, the human knee may be subjected to a variety of damaging stresses and strains particularly during running and jumping movements. Athletes, in particular, are apt to incur a knee injury as a result of a blow to the knee or to a twisting of the knee, which can commonly occur in various contact sports or high stress sports, such as football, basketball, or skiing.

There are a variety of knee braces available on the market or through healthcare providers. These range from braces that attempt to totally immobilize the knee, to functional braces that may be as simple as flexible elastic bandages that are intended to provide some flexibility while eliminating lateral movement of the ligaments that support the knee. Some of these products are intended to be worn as a relatively permanent device for long-term wear while others are intended to be worn for a short period of time to support a weakened knee during strenuous activities. These functional braces have as their primary object to allow for bending of the knee while preventing any unnatural movement that may aggravate the knee ligaments. Some braces are meant to provide a constant or variable "unloading" force on the knee joint to alleviate pain, such as pain caused by osteoarthritis. While functional braces are intended to allow for a natural movement of the knee joint while a person undergoes walking, running, jumping, skating, etc., they are also intended to prevent sudden movement of the upper and lower legs to one side or the other and to prevent twisting or rotation of the lower leg relative to the upper leg about the vertical axis, and/or to provide a pain-relieving force to the joint.

FIG. 1A is a fragmentary perspective view of a knee brace 105 mounted onto the leg 110 of a person/patient. In one embodiment, the brace 105 is intended to control movement of the thigh to protect the ACL against excessive rotation or extension. In one embodiment, the brace 105 is a closed-loop system that provides electrical muscle stimulation (EMS) based on feedback received from the brace 105. The feedback may be based on the applied EMS and the knee's response to the EMS. The feedback can be any combination of types of feedback.

The brace 105 includes a proximal end 120 and a distal end 125. The proximal end 120 is typically in physical contact with the person's femur. The distal end 125 is typically in physical contact with the person's tibia. The brace 105 is shown as having an opening at the knee 115. Although shown with an opening, the brace 105 can alternatively be closed at the knee 115.

In one embodiment, the proximal end 120 and distal end 125 of the brace 105 are connected by a pivotal joint or hinge 130. The pivotal joint 130 enables the brace 105 to flex at the joint 130 when the person bends his or her knee 115. As described in more detail below, in one embodiment the pivotal joint 130 includes a digital positional encoder 135 which determines an absolute position of the knee 115. The positional encoder 135 can provide this position of the knee 115 to the brace 105 digitally as part of the feedback in order for the brace 105 to record the position (or, in another embodiment, adjust) based on the transmitted position. Although the brace 105 is shown with one pivotal joint 130, the brace 105 can also include a second pivotal joint on the other side of the brace 105 which connects the other side of the proximal end 120 to the other side of the distal end 125. Brace 105 can be made from any of a variety of materials, such as from combinations of metal, foam, plastic, elastic material, composits, and straps.

The brace 105 can be secured to the person's body via one or more connectors 140, 150. In one embodiment, connectors 140, 150 are straps that connect to the brace 105 or to the respective connector 140, 150 itself. Although shown with two connectors 140, 150, any number of connectors may be used. Connectors 140, 150 may be bolts, screws, pins, velcro, strings, clamps, or any other suitable connectors.

Figure 1B:
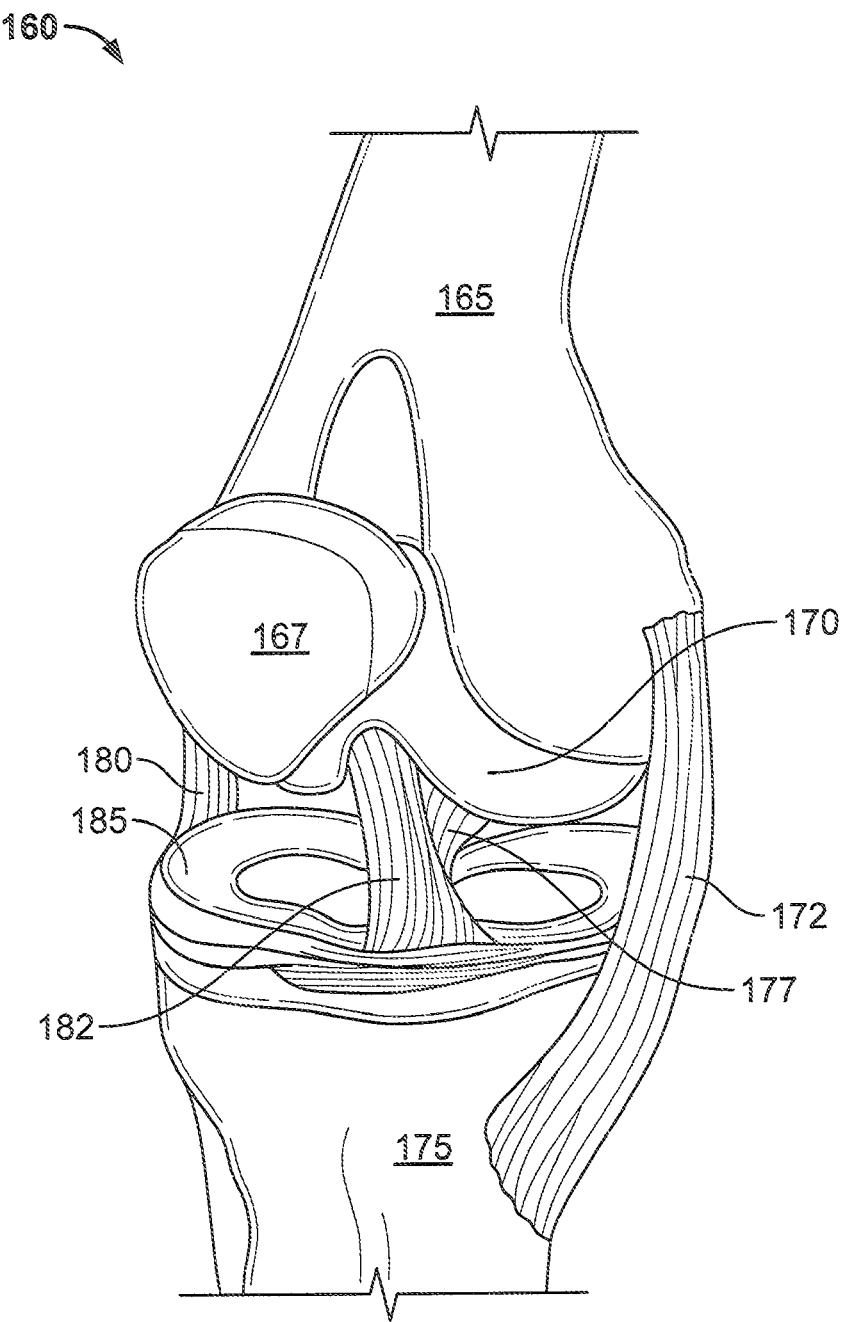
FIG. 1B is a perspective view of a knee joint.

FIG. 1B shows a perspective view of the knee joint 160. The femur 165 or thigh bone 165 connects to the patella 167 or kneecap. Articular cartilage 170 lines the bones, cushioning the joint. The medial collateral ligament (MCL) 172 runs down the inside of the knee joint and connects the femur 165 to the tibia 175 (shinbone). The MCL limits the sideways motion of the knee. The posterior cruciate ligament (PCL) 177 also connects femur 165 and tibia 175. The PCL 177 limits backward motion of the tibia 175. The lateral collateral ligament (LCL) 180 runs on the outside of the knee. The LCL limits sideways motion. The anterior cruciate ligament (ACL) 182 connects the femur 165 to the tibia 175 in the center of the knee. The ACL 182 limits rotation and the forward motion of the tibia 175. The meniscus 185 is cartilage that absorbs shock in the joint 160.

Figure 2:
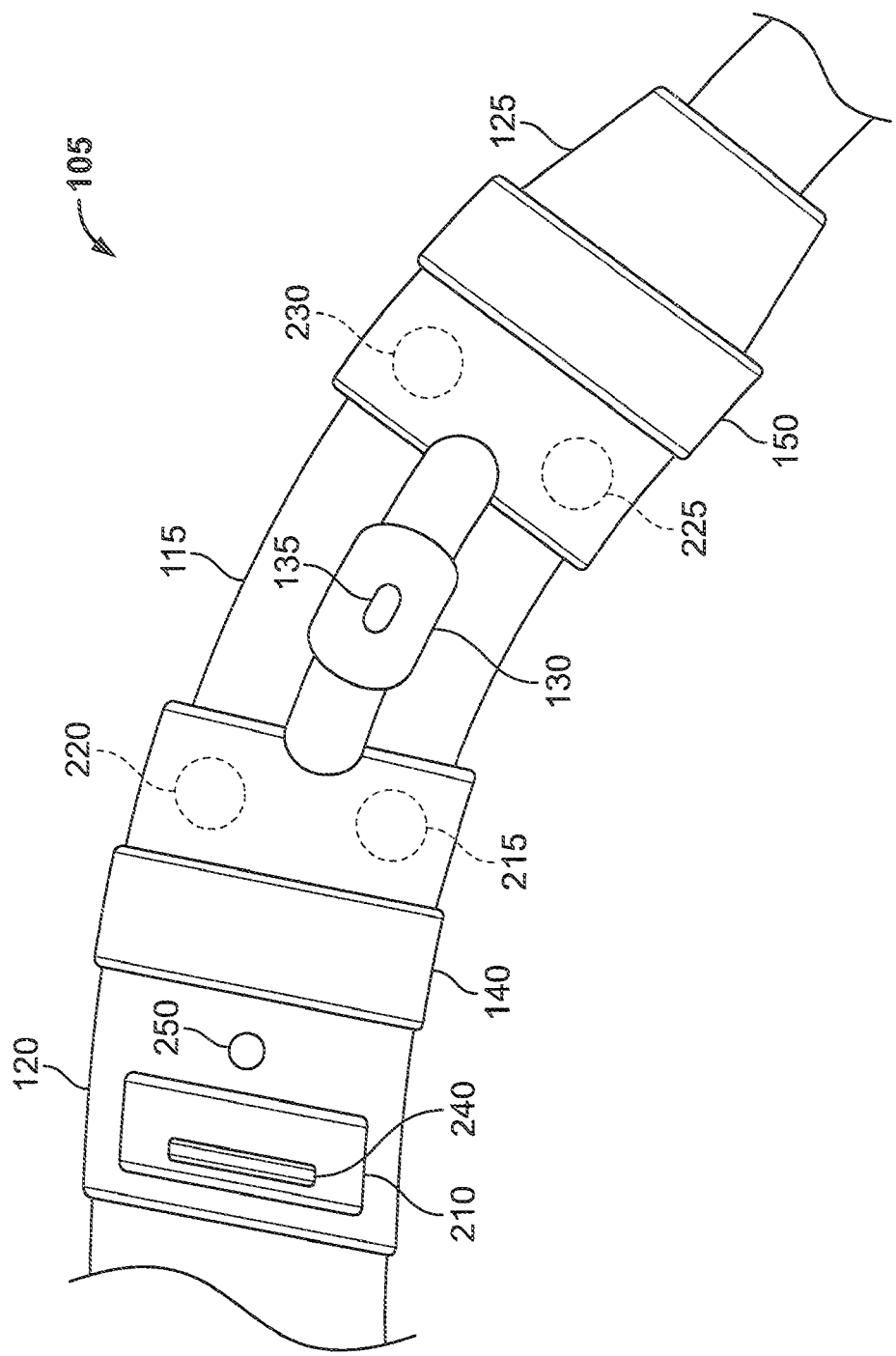
FIG. 2 is a more detailed fragmentary perspective view of a knee brace mounted onto the knee of a patient in accordance with an embodiment of the disclosure.

Also referring to FIG. 2, brace 105 includes control electronics 210 attached to or embedded within the brace 105. Although shown as being located in the proximal end 120 of the brace 105, control electronics 210 can be embedded within any location of the brace 105, such as within the distal end 125 of the brace 105, within the pivotal joint 130, and/or within one or more of the connectors 140, 150. Further, the control electronics 210 can be attached to the brace 105 via one or more cables or wires. In one embodiment, one or more of the components of the control electronics 210 is removable from the brace 105.

In one embodiment, the control electronics 210 enable EMS of one or more muscles that are in contact with the brace 105. Specifically, the brace 105 includes one or more sensors/pads/electrodes (e.g., sensor 215, 220, 225, 230) positioned in specific locations throughout the brace 105. Although the brace 105 shown in FIG. 2 includes two sensors 215, 220 positioned in the proximal end 120 of the brace 105 and two sensors 225, 230 positioned in the distal end 125 of the brace 105, the sensors 215, 220, 225, 230 can be in any configuration at any location. Further, although brace 105 is shown with four sensors 215, 220, 225, 230, any number of sensors (e.g., six sensors) can be used. Additionally, the sensors 215, 220, 225, 230 may be any shape and any size, such as a circular shape or an oval shape. Additionally, the sensors 215, 220, 225, 230 may be moveable (e.g., positioned in the brace but moveable by the doctor or patient). For example, the sensors 215, 220, 225, 230 can be moved within a circle/diameter of approximately 3 inches. In one embodiment, the sensors 215, 220, 225, 230 are moveable but are secured with a strong Velcro material. In one embodiment, the sensors are electrodes or electrical contacts that can transmit and/or respond to voltage, current, and/or power. In one embodiment, the sensors are passive-they do not include an amplifier or any processing means.

In one embodiment, sensors around the knee are to be positioned as follows: 1) The motor point of the vastus medialis oblique, 2) The motor point of the vastus lateralis, and 3) the motor point of the distal central hamstring. In one embodiment, there are no sensors or electrodes positioned on the calf muscles.

In one embodiment, the sensors 215, 220, 225, 230 are located on the interior wall of the brace 105 so that the sensors 215, 220, 225, 230 come in contact with the person's skin. Each sensor 215, 220, 225, 230 can take a power dissipation reading on the person's human tissues to determine how much the control electronics 210 "shocks" the person (i.e., how much current or voltage or power the sensors 215, 220, 225, 230 produce/apply to the person's human tissues). In one embodiment, galvanic skin resistance can be determined from the power dissipation reading. The majority of the human body's resistance is in the skin—the dead, dry cells of the epidermis (the skin's outer layer) are usually poor conductors. Depending on the person, the resistance of dry skin is usually between 1,000-100,000 Ohms. The skin's resistance is lower if the skin is wet with an electrolytic solution (e.g., from sweat or from moisture). Conventional sensors apply a constant current to a person's skin based on an assumption of 500 Ohms of resistance for the person's skin. Unlike conventional sensors, the sensors 215, 220, 225, 230 of the brace 105 measure the power dissipation of the human tissues of the person and adjust the output current/voltage/power based on this measurement. Thus, the quantity of electricity output by one or more of the sensors 215, 220, 225, 230 is based on an electrical reading of the person's human tissues. In one embodiment, the reading occurs when the person's skin creates a closed circuit across two sensors (e.g., sensors 215, 220 or sensors 225, 230). For example, when a person wears the brace 105, the person's skin on his or her leg closes the circuit between sensor 215 and sensor 220, thereby enabling a power factor reading to occur. Once this reading is transmitted to the control electronics 210, the electronics 210 adjusts the current/voltage/power output produced by the sensors to stimulate the muscles in the person's leg.

In one embodiment, the sensors 215, 220, 225, 230 measure the patient's power dissipation factor periodically after a predetermined time period has elapsed (e.g., every 5 ms). In another embodiment, a medical professional can instruct the control electronics 210 to take a reading at a certain time or for a given amount of time (e.g., measure power dissipation every 5 ms from 6 PM to 7 PM). The medical professional or the brace 105 itself can also be programmed to "shock" the patient at a predetermined time or times or on a specific schedule.

Further, conventional sensors or pads typically require the use of an electrolytic gel to facilitate conduction of the current/voltage/power output by the pads. Unlike conventional sensors, the sensors 215, 220, 225, 230 in one embodiment are not used with gel. Instead, the sensors 215, 220, 225, 230 are conductive silicon material that creates an electrical connection with a person's human tissues (e.g., via sweat, moisture, or skin itself). In one embodiment, the sensors 215, 220, 225, 230 are silicon with a conductive material (e.g., a metal) impregnated into the silicon, such as silicon nickel. Other conductive materials may be used, such as aluminum and/or carbon particles. In one embodiment, the electrode pad is a carbon filled silicone sheet from Stockwell elastomerics, part No. SE 65-CON.

Additionally, many conventional pads stick to the patient's skin in order to make adequate contact with the skin. This causes problems, such as that the stickiness of the pad will cause hair or skin to be removed when the pad is removed or moved (e.g., as the brace moves or bends). Unlike these conventional sensors, in one embodiment sensors 215, 220, 225, 230 do not use any sticky substance to connect to the patient's skin. Instead, the sensors 215, 220, 225, 230 can make physical contact with the human tissues (e.g., skin) via the placement of the sensors 215, 220, 225, 230 in the brace 105. In another embodiment, the sensors 215, 220, 225, 230 are used with gel. In one embodiment, the system can run both types of pads-pads with gel and pads without gel.

The control electronics 210 receives feedback from one or more of the sensors 215, 220, 225, 230 and/or the positional encoder 135, thereby forming a closed loop system. Specifically, the brace 105 delivers EMS to the muscle via one or more of the sensors 215, 220, 225, 230 and adjusts the amount of current/voltage/power delivered by one or more of the sensors 215, 220, 225, 230 based on the readings obtained by the sensors 215, 220, 225, 230 and communicated to the control electronics 210.

In one embodiment, the control electronics 210 includes a microprocessor (e.g., ARM® CORTEX™ microprocessor developed by ARM® Ltd. of San Jose, CA) with one or more batteries and a communications module such as a Bluetooth transceiver/module. The control electronics 210 can provide stimulation via the sensors 215, 220, 225, 230 via any type of waveform or signal, such as a parabolic arc (e.g., start soft and progressively increase), sine wave, cosine wave, pulse width modulation (PWM), pulse density modulation (PDM), square wave, sawtooth wave, etc. Further, the control electronics 210 can provide waveforms with any pulse duration and any pulse width.

In one embodiment, the sensor and the electrical stimulation electrode share a common contact point. In on embodiment, a MOSFET is included to build a switch between two phases—one phase is completely isolated from the other phase. As a result of that isolation combined with knowing how much energy has been put into the system, an accurate reading of the power dissipation can be obtained. To determine when to input a sensing pulse versus when to input a stimulation pulse, it is known what is input in the stimulation pulse, and then the control electronics 210 inputs a sense pulse with higher voltage. Because a higher voltage was input in the sense pulse, however, any residual voltage from the stimulation phase doesn't matter because the voltage has been raised up to a new level to do the sensing phase. Thus, before taking a reading of the power dissipation, the voltage is automatically raised. If the voltage was not raised, then residual voltage would be obtained/read from the stimulation pulse. This therefore eliminates dealing with the residual voltage. This is how the control electronics 210 gets around the capacitance and voltage in tissue. The control electronics 210 raises the voltage of the entire area, and eliminates the problem of residual voltage and can then determine power dissipation.

In a further embodiment, the control electronics 210 adjusts the current/voltage/power delivered to the sensors 215, 220, 225, 230 based on feedback from the positional encoder 135 and/or the sensors 215, 220, 225, 230. In one embodiment, one or more of the sensors 215, 220, 225, 230 behave differently depending on the position of the knee. Additionally, the power loss varies for every person and changes during the course of operation, and the control electronics 210 can repeatedly measure the power dissipation of the patient via the sensors 215, 220, 225, 230 and repeatedly adjust the output current/voltage/power based on these readings. Thus, in one embodiment, a medical professional may set the brace to level 3 stimulation for person A because person A has sensitive skin, and may set the brace to level 6 stimulation for person B because person B has "thick" skin and is not as sensitive to the stimulation. In another embodiment, the level stimulation is set automatically based on the feedback. In yet another embodiment, the patient sets the level stimulation via a knob or control on the brace 105.

In one embodiment, the signals input by the control electronics 210 are constant current signals and providing variable voltage to attempt to maintain constant power output. In one embodiment, the current and/or voltage is varied to attempt to deliver constant power. In one embodiment, the control electronics 210 inputs a test signal first (e.g., 200 volts) (e.g., sense pulse identified above) to break down the dielectric constant of the human tissues before inputting each stimulation signal. This test signal creates an ionized channel or a channel of higher conduction. After the test pulse is input into the human tissues, the stimulation pulse is input into the human tissues, which enables the stimulation pulse to have a lower voltage and therefore a lower total power. The stimulation pulse is adjusted based on the readings from the test pulse. Thus, the control electronics 210 measures the power dissipation before every stimulation pulse. This test pulse is why, if an electrical open circuit is detected or an electrical short is detected (e.g., if the patient falls into water), the stimulation pulse does not fire.

As described in more detail below, the brace 105 may communicate data generated by the control electronics 210 and/or the feedback provided by the sensors 215, 220, 225, 230 and/or the positional encoder 135 to a medical professional (e.g., doctor, surgeon, and/or physical therapist). The medical professional may adjust the brace 105 based on this data. For example, the brace 105 may measure how strong the muscles surrounding the knee 115 are getting based on the EMS and/or the range of motion of the knee 115 (obtained via the positional encoder 135). As described in more detail below, the medical professional can utilize this feedback and data to adjust the treatment of the patient. For example, the medical professional may adjust the brace 105 based on these readings. Thus, brace 105 provides a combination of bracing a joint and simultaneously stimulating the muscle(s) around the joint.

Additionally, athletes or coaches may be interested in statistics produced by the control electronics 210, such as determining how much an athlete's joint can move after an injury or during recovery. As a specific example, a pitching coach on a baseball team is likely interested in statistics associated with a pitcher's movement of his pitching arm.

In one embodiment, the control electronics 210 includes one or more control programs that a medical professional or patient can select and/or program. The control programs may be dynamic (e.g., changeable or variable, not a fixed frequency, not fixed timing, not a fixed waveform, etc.) and may cause different types of EMS to be executed on different parts of the patient's body. For example, if the feedback data from the control electronics 210 indicates that the patient's vastus medialis oblique muscles are getting stronger while the patient's distal central hamstring (or, in another embodiment, the patient's calf muscle) is not getting stronger, a medical professional (e.g., doctor or physical therapist) may instruct, via one or more of these programs, the brace 105 to execute a predetermined control program. This predetermined control program may cause sensors 215, 220 to output a current of 7 mA of DC current for 30 seconds and then 5 mA for 20 seconds. The predetermined control program may further cause sensors 225, 230 to output a current of 1 mA for 50 seconds, thereby providing significantly more stimulation to the patient's vastus medialis oblique muscles compared with the patient's distal central hamstring (or, in another embodiment, the patient's calf muscle). In one embodiment, the brace 105 includes specific programs for the first week after surgery, specific programs for the first month after surgery, specific programs for arthritis, etc.

In one embodiment, the brace 105 includes an authentication button 250. The authentication button 250 is a button that has to be pressed by the patient in order for a program to execute. Thus, the authentication button 250 is a security feature of the brace 105—the brace 105 cannot be compromised or caused to execute one or more stimulation programs or actions until the wearer of the brace presses the authentication button 250. For example, if a medical professional remotely accesses the control electronics 210 and attempts to have the brace 105 execute specific muscle stimulation or adjust the range of motion of the brace 105 for the patient, the brace 105 will not execute the stimulation or adjust the range of motion until the patient presses the authentication button 250.

The control electronics 210 may also include a display 240. The display 240 may display statistics associated with the brace, such as how much power dissipation the sensors 215, 220, 225, 230 are measuring, how much current/voltage/power the sensors 215, 220, 225, 230 are delivering, the angle of the positional encoder 135, programs executing or past programs executed, the date, the time, the patient's next appointment (e.g., with a doctor or a physical therapist), average range of motion of the joint over a fixed period of time or any other information associated with the brace 105. In one embodiment, the control electronics 210 includes a keyboard to enable the user to provide input to brace 105.

The brace 105 may also have visual feedback. For example, one or more LEDs can be located on the brace 105 for alerting the patient of a specific occurrence. For instance, an LED can light when the brace 105 is waiting for the patient to press the authentication button 250.

Additionally, the brace 105 may transmit the generated data (feedback data) to a computing device associated with, for example, the user or the medical professional. Due to the communication of the brace 105 with the computing device, the medical professional can be notified or will see that the patient is not wearing the brace if an electrical open circuit is detected. Similarly, if the patient falls into a pool, the medical professional will know this as well because an electrical short is detected.

In one embodiment, the medical professional or brace 105 can transmit the data generated by the brace 105 to an insurance company. The insurance company can then determine, from this data, whether the patient is performing his or her exercises, is wearing the brace throughout the day, etc. This may affect the insurance provided by the insurance company (e.g., lower premium if patient wearing brace all day and doing exercises). In one embodiment, medical professionals such as doctors may request or obtain a specific insurance reimbursement when prescribing the brace. In one embodiment, a specific insurance code may be available to the medical professional for prescribing the brace.

In one embodiment, the brace 105 is an unloader brace. Unloader braces are usually prescribed for people who have medial (inner part of the knee) compartment knee osteoarthritis. These knee braces unload stress from the affected joint by placing pressure on the thigh bone. This forces the knee to bend away from the painful area. Thus, an unloader brace is a brace that is stronger and more rigid on one part of the knee. In one embodiment, brace 105 exerts a force on one direction of the knee. In one embodiment, an adapter piece attaches to the brace 105 to exert such a force, thereby forming an unloader brace.

The brace 105 may also be configured to provide co-coupled contraction of different muscle groups. For example, four sensors (e.g., including sensors 215 and 220) can be located on the quadriceps muscles and two sensors (e.g., sensors 225 and 230) can be located on the hamstring muscles. The brace 105 can stimulate both sets of muscles at different times or simultaneously, such as at the same or at different frequencies, patterns, and/or waveforms. For example, when the brace 105 activates or fires the sensors 215, 220 at a first rate, the brace 105 can activate or fire the sensors 225, 230 at a second, slower rate (or, in another embodiment, at the same rate). The firing of the hamstring at a different frequency than (or at the same time as) the quadriceps muscles results in co-coupled contraction. The firing of the hamstring (the antagonistic muscle group) with the quadriceps muscles results in the strengthening of both sets of muscles. The stimulation of the antagonistic muscle group strengthens both sets of muscles, even when only one of the muscle groups is atrophied. In one embodiment, the brace 105 can be programmed to execute a first program for a first muscle and execute a second program for a second, antagonistic muscle. In one embodiment, the doctor positions the sensors 215, 220, 225, 230 on the brace 105 for this co-coupled contraction to occur. In another embodiment, the sensors 215, 220, 225, 230 are integrally positioned within the brace 105 to cause the co-coupled contraction of different muscle groups.

In one embodiment, the brace 105 includes a data gathering thermometer which can determine the temperature of the patient and adjust one or more of the sensors 215, 220, 225, 230 and/or the control electronics 210 based on this temperature.

Figure 3:
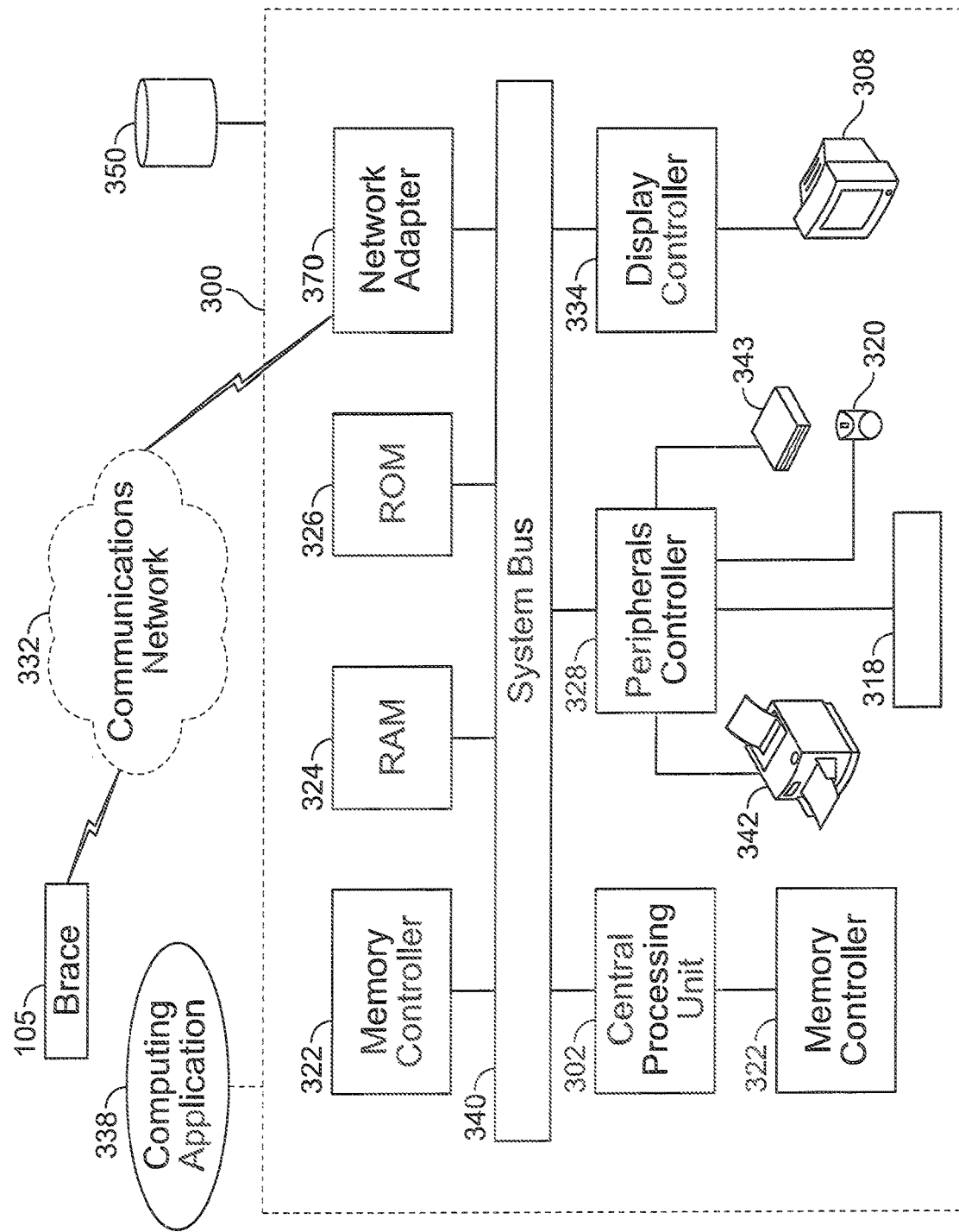
FIG. 3 is a block diagram of the knee brace of FIG. 1 in communication with a computing device in accordance with an embodiment of the disclosure.

Referring to FIG. 3, the brace 105 (control electronics 210) can be configured to communicate (e.g., wirelessly or via a wired connection) with a computing device 300. Examples of the computing device 300 include, but are not limited to, personal computers, digital assistants, personal digital assistants, mobile phones, smartphones, tablets, or laptop computers. The computing device 300 may be the patient's device or a device associated with a medical professional. This can enable the medical professional to retrieve and analyze data transmitted from the brace 105. In one embodiment, this data is transmitted in real-time, so that the medical professional can analyze the data and/or adjust the brace 105 at any time.

Computer device 300 is a logic apparatus adapted and configured to read instructions from media and/or a network port. Computing device 300 can be connected to the Internet or an intranet. The device 300 includes a central processing unit (CPU) 302, one or more memory (e.g., RAM 324 and/or ROM 326), optional input devices, illustrated as keyboard 318 and/or mouse 320 and optional monitor 308. In one embodiment, the computing device 300 is in communication with or is a server computer. The computing device 300 can include any suitable means of transmitting and/or receiving data. For example, the computing device 300 can have a network connection, a wireless connection or an internet connection. It is envisioned that data relating to the present disclosure can be transmitted over such networks or connections.

The computing device 300 is capable of, or in at least some situations adaptable for, executing a variety of computing applications 338, including computing applications, a computing applet, a computing program, or other instructions for operating on computing device 300 to perform at least one function, operation, and/or procedure. Computing device 300 is controllable by computer readable storage media for tangibly storing computer readable instructions, which may be in the form of software. The computer readable storage media capable of, or in at least some situations adaptable to, tangibly store computer readable instructions can contain instructions for computing device 300 for storing and accessing the computer readable storage media to read the instructions stored thereon themselves. Such software may be executed within CPU 302 to cause the computing system 300 to perform desired functions.

As will be appreciated by those skilled in the art, a computer readable medium stores computer data, which data can include computer program code that is executable by a computer, in machine readable form. By way of example, and not limitation, a computer readable medium may comprise computer readable storage media, for tangible or fixed storage of data, or communication media for transient interpretation of code-containing signals. Computer readable storage media, as used herein, refers to physical or tangible storage (as opposed to signals) and includes without limitation volatile and non-volatile, removable and non-removable storage media implemented in any method or technology for the tangible storage of information such as computer-readable instructions, data structures, program modules or other data.

Computer readable storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other physical or material medium which can be used to tangibly store the desired information or data or instructions and which can be accessed by a computer or processor.

In operation, the CPU 302 fetches, decodes, and executes instructions, and transfers information to and from other resources via the computer's main data-transfer path, system bus 340. Such a system bus connects the components in the computing device 300 and defines the medium for data exchange. Access to the RAM 324 and/or ROM 326 may be controlled by memory controller 322. The memory controller 322 may provide an address translation function that translates virtual addresses into physical addresses as instructions are executed.

In addition, the computing device 300 can contain peripherals controller 328 responsible for communicating instructions from the CPU 302 to peripherals, such as, printer 342, keyboard 318, mouse 320, and data storage drive 343. Display 308, which is controlled by a display controller 334, is used to display visual output generated by the computing device 300. Such visual output may include text, graphics, animated graphics, and video. The display controller 334 includes electronic components required to generate a video signal that is sent to display 308. Further, the computing device 300 can contain network adaptor 336 which may be used to connect the computing device 300 to an external communications network 332.

By way of example, Bluetooth products may be used to provide links between brace 105 and mobile computers, mobile phones, portable handheld devices, personal digital assistants (PDAs), tablets, and other mobile devices and connectivity to the Internet. Bluetooth is a computing and telecommunications industry specification that details how mobile devices can easily interconnect with each other and with non-mobile devices using a short-range wireless connection.

The computing device 300 may utilize a specific application 338 (also referred to as an "app") to communicate with and/or program the brace 105. In one embodiment, the computing device 300 downloads the app 338 from the communications network 332 (e.g., from an "app store" on the Internet). The app 338 may provide statistics, graphs, normalized data, raw data, averages (e.g., average flexion and average extension), real-time data, etc. to the medical professional. In one embodiment, the app 338 provides output data that is in a format customized by the user or medical professional. In one embodiment, the app 338 communicates with other programs, such as hospital software, word processing software (e.g., Microsoft Word®), spreadsheet software (e.g., Microsoft Excel®), email software (e.g., Microsoft Outlook®), publishing software (e.g., Microsoft Powerpoint®), etc. (e.g., to further analyze or display the data). The app 338 may provide a graphical user interface (GUI) or a text-based user interface. The app 338 communicates with the brace 105 and/or a database (as described below) to display and analyze the data generated by the brace 105 (and/or doctor). In one embodiment, the app 338 can program the brace 105, such as by the patient or the doctor. In one embodiment, and as described above, the patient has to press the authentication button 250 in order for the brace 105 to actually execute the program being set remotely.

In yet another embodiment, the computing device 300 is a portable data reader that is specifically associated with the brace 105. For example, a medical professional can synchronize the reader 300 with the patient's brace 105 when the medical professional provides the brace 105 to the patient. At some later time (e.g., at a subsequent visit), the medical professional can use the reader to capture data from the brace 105. The medical professional can then use the reader to view the retrieved data (during the patient's visit and/or before the visit).

In at least some configurations, a user executes a browser to view digital content items and can connect to a server via a network, which is typically the Internet, but can also be any network, including but not limited to any combination of a LAN, a MAN, a WAN, a mobile, wired or wireless network, a private network, or a virtual private network.

In one embodiment, the computing device 300 is in communication with a database 350. The computing device 300 may store data transmitted by the brace 105 in database

350. The database 350 may be an internal database of the computing device 300. Alternatively, the database 350 may be an external database in communication with the computing device 300.

To protect patient confidentiality and to protect the security of the data, usage data that is transmitted from the devices (via Bluetooth, WiFi, or via other means) is encrypted to ensure that only the patient or the patient's doctor can obtain access to this medical information. The encryption can be done via either software executing on the processor or via external hardware that processes the data before it is transmitted. In one embodiment, each set of logs is uniquely tied to the device that created them. This can be done by the device tagging the data being transmitted from the device with a unique identifier associated with the device itself. The unique identifier is set either by the processor or by an external component of the system (e.g., UUID chip).

The database 350 can be used by, for example, doctors or medical professionals to retrieve, review, and/or analyze the data from the brace 105. The doctors may utilize the data from the brace in the doctor's analysis or recommendations to the patient. Further, doctors may utilize the data from the brace 105 of one patient in recommendations to other patients with similar conditions or injuries. For example, if the doctor tells a patient recovering from an ACL reconstructive surgery to execute program 1 for the first week and to execute program 2 for the second week, and if the doctor sees significant improvements in the patient's strength in the patient's knee due to these programs, the doctor will likely tell another patient recovering from a similar surgery to execute the same programs during the same time periods. The doctor can then obtain data from both patients to see how they are responding to the brace 105 and the programs being executed by the brace 105.

In one embodiment, the brace 105 includes a distress or panic button. When pressed, the distress/panic button may notify a medical professional (e.g., doctor) or service that the patient needs assistance (e.g., has fallen and has hurt himself). The medical professional or service can then travel to the patient's location to assist the patient or call the patient to determine what is wrong. In one embodiment, the pressing of the panic/distress button results in a flag being set at the given time in the data. The flag may indicate what EMS was being executed, etc. This flag may also indicate to the medical professional that the patient did not perform his or her EMS treatment at a previously designated time.

Figure 4:
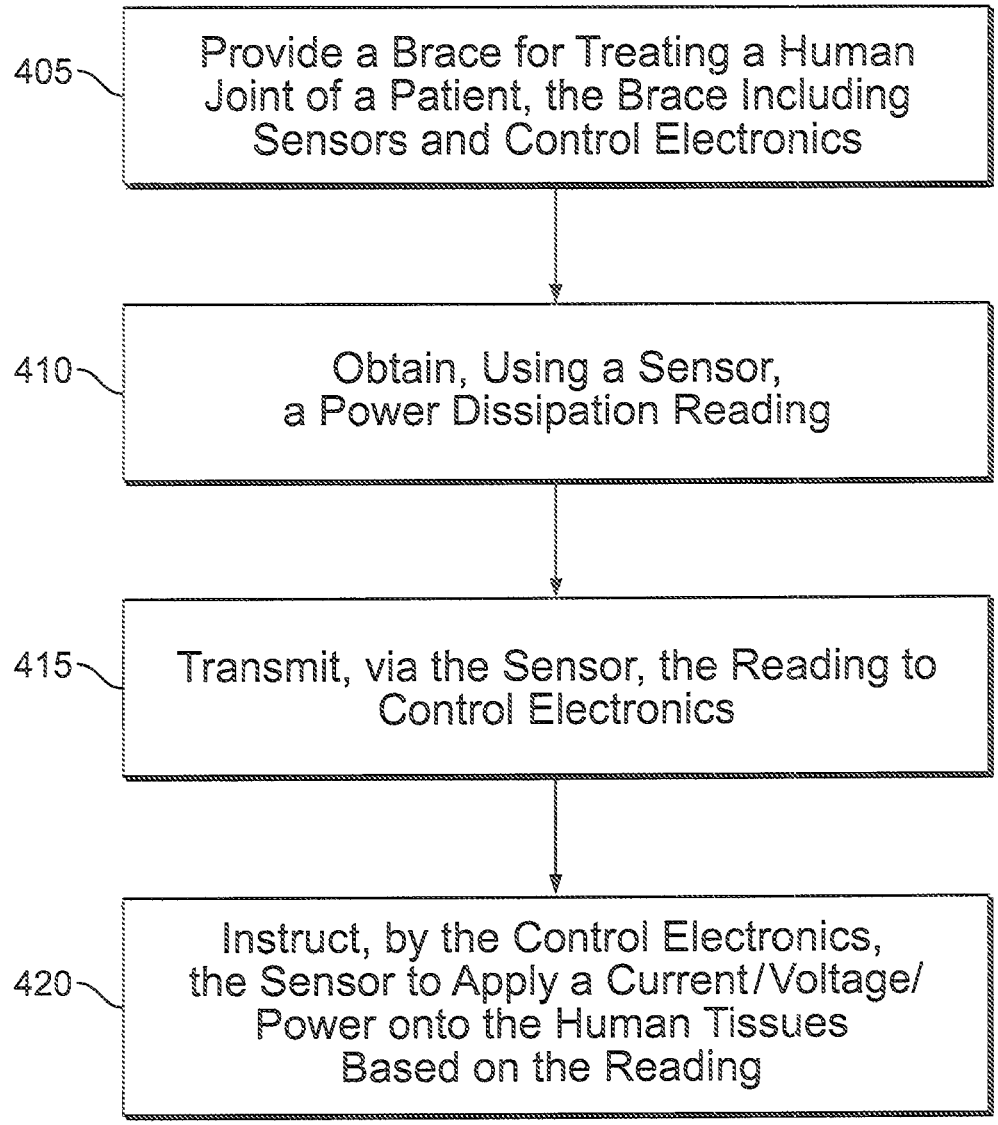
FIG. 4 is a flow diagram of an example of steps performed according to an embodiment of the disclosure.

FIG. 4 shows a flowchart illustrating an embodiment of steps performed in the closed loop feedback bracing system. A brace is provided for treating a human joint of a patient (e.g., knee, elbow, back, spine, wrist, etc.) (Step 405). The brace includes sensors and control electronics. One or more sensors 215, 220, 225, 230 obtain a power dissipation reading (Step 410). As described above, in one embodiment two sensors obtain a power dissipation reading when skin completes the circuit between the two sensors. The sensor or sensors 215, 220, 225, 230 then transmit the power dissipation reading to the control electronics 210 (Step 415). The control electronics 210 instruct the sensor or sensors 215, 220, 225, 230 to apply a current/voltage/power onto the human tissues based on the power dissipation reading (Step 420). This results in a closed loop feedback system, where the output of the brace 105 is dependent upon the input readings of power dissipation (e.g., of sweat, of human tissues, etc.). In one embodiment, the output of the brace 105 is dependent upon the input readings of power dissipation from the sensors 215, 220, 225, 230.

Figure 5:
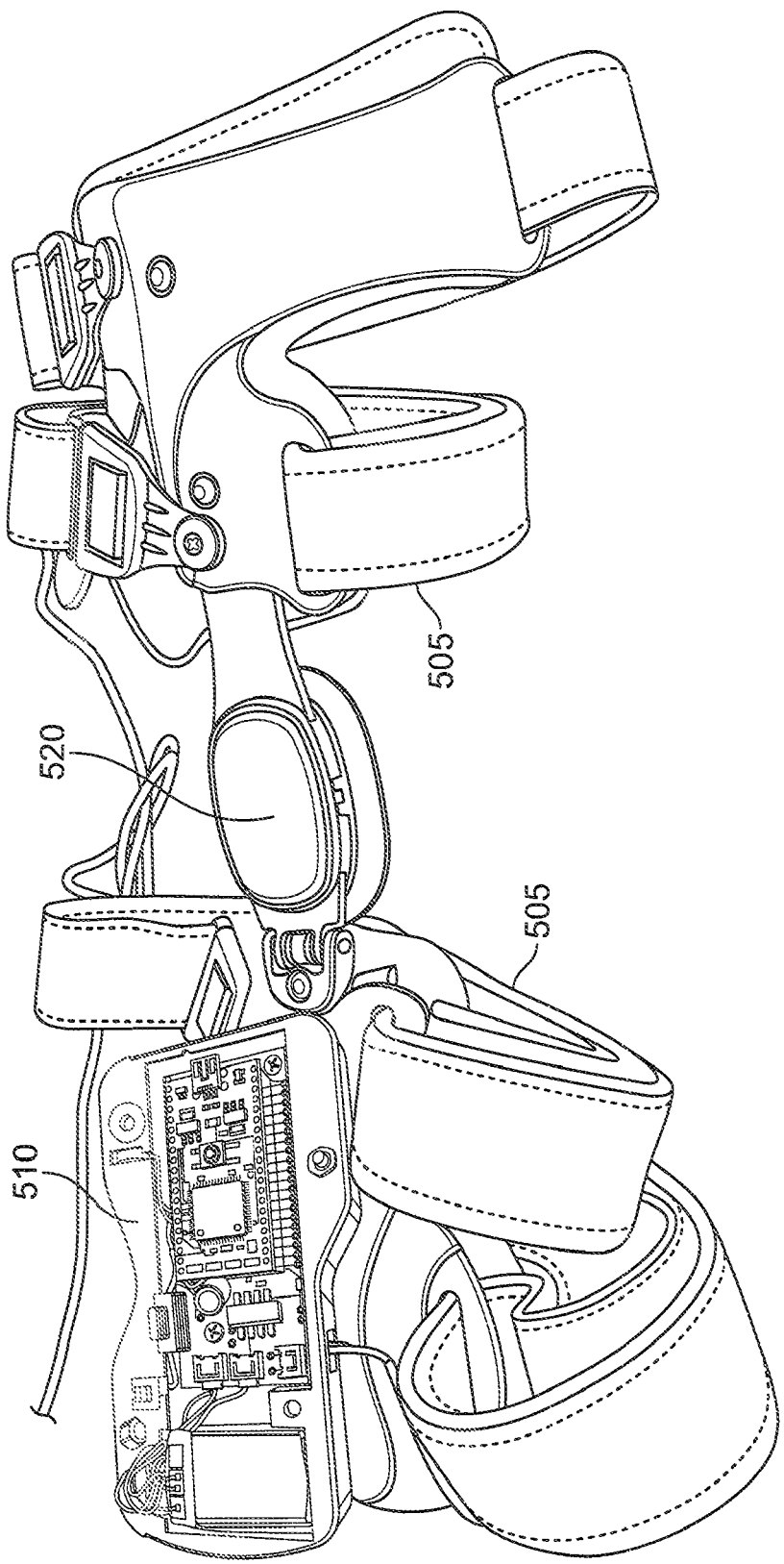
FIG. 5 is a perspective view of a knee brace according to an embodiment of the disclosure.
Figure 6:
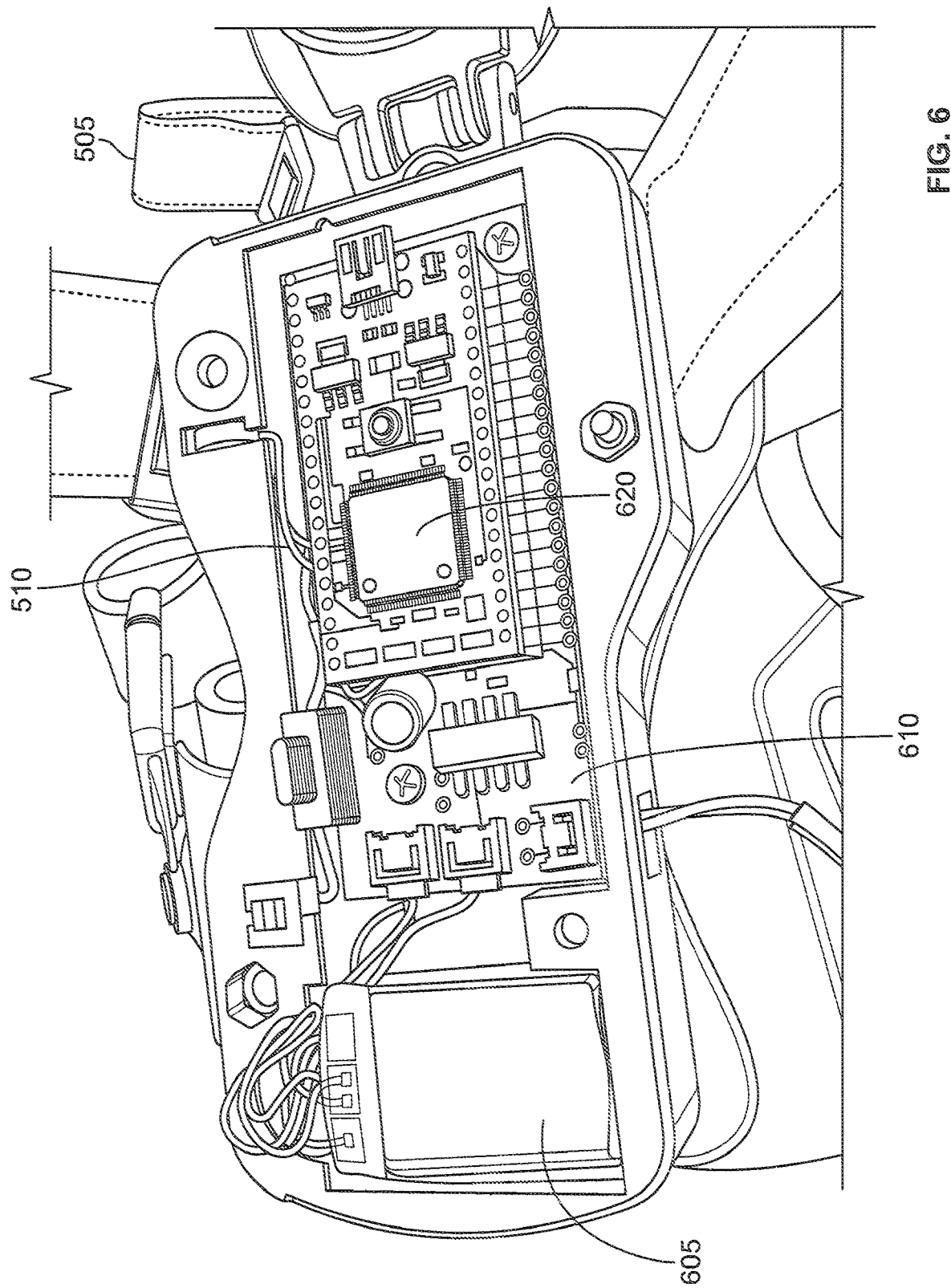
FIG. 6 is a perspective view of control electronics of a knee brace according to an embodiment of the disclosure.
Figure 7:
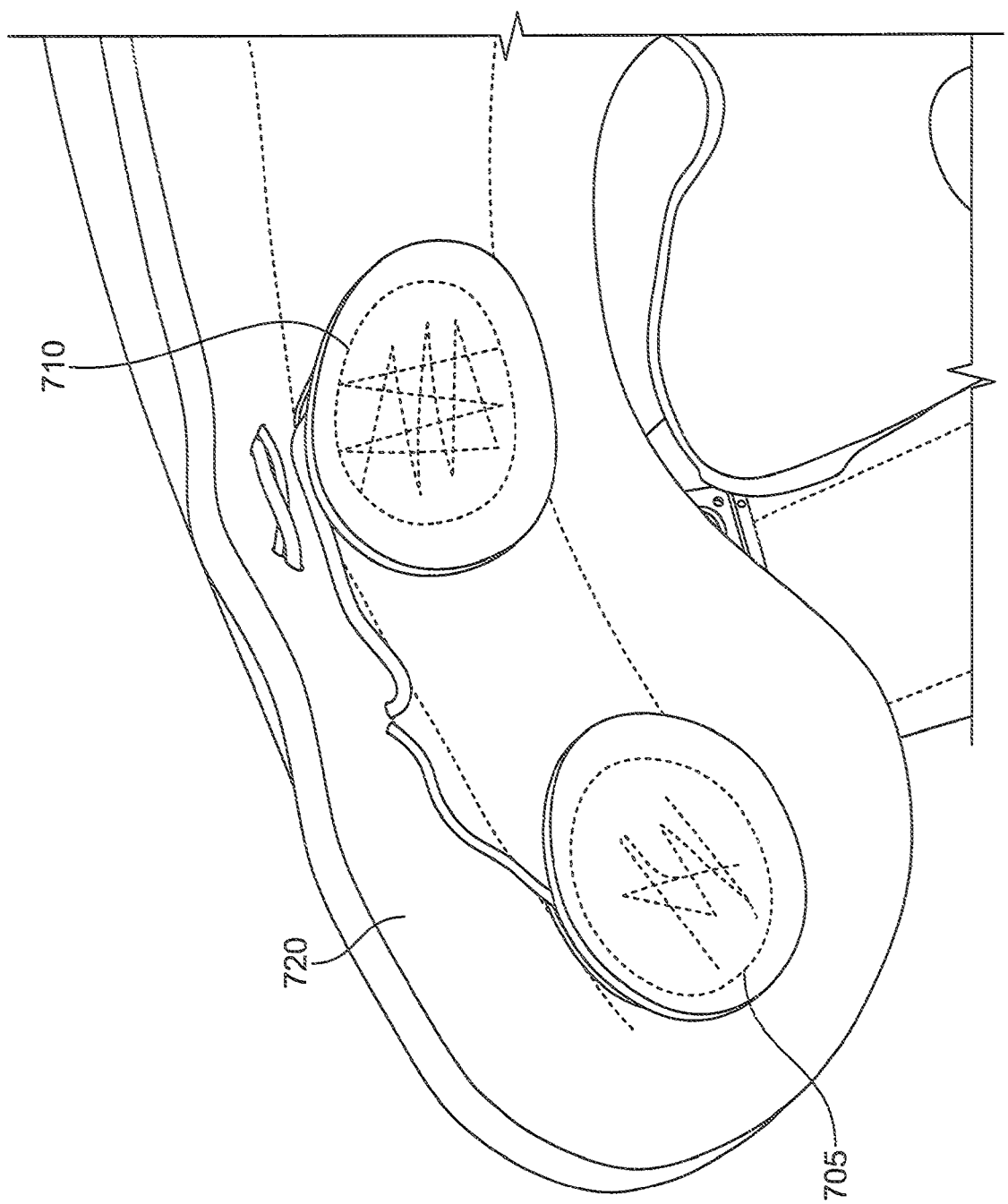
FIG. 7 is a perspective view of sensors of the knee brace according to an embodiment of the disclosure.

FIG. 5 is a perspective view of an embodiment of a knee brace 505 including control electronics 510 and a pivotal joint 520. FIG. 6 is a more detailed perspective view of control electronics 510 of the knee brace 505. The control electronics 510 include a battery 605 connected to a circuit board 610. The circuit board 610 includes a microprocessor 620 for the programming of and functioning of the brace 505. FIG. 7 is a perspective view of two sensors 705, 710 of the knee brace 720. The sensors 705, 710 are located on the interior wall of the brace 720 so that the skin of the wearer of the brace is in physical contact with the sensors 705, 710.

In one embodiment, the brace enables the patient to move the joint (e.g., knee) while wearing the brace and while the sensors are providing EMS and obtaining the power dissipation of the patient's human tissues. The brace can cross the joint (e.g., knee) and still enable motion by the patient because there is no sticky adhesive used with the sensors. Thus, in one embodiment, the brace enables providing EMS while the patient is doing physical therapy or exercising.

In one embodiment, a control unit connects to the brace and controls or programs the brace. In one embodiment, some or all of the control electronics are located in the control unit and not in or on the brace. For example, the control unit may connect to (e.g., wirelessly or via one or more wires) and communicate with the sensors. The control unit can program the sensors to run specific programs, can receive the power dissipation from the sensors, and can adjust the EMS based on the received readings. In one embodiment, the brace includes a memory chip that stores the program(s) associated with the specific brace, such as the waveforms applied to the brace at specific times. When the control unit connects to the brace, the control unit can read the program(s) from the memory chip on the brace and communicate with the sensors to run the read program. In one embodiment, the control unit reads an identifier from the brace to identify the type of brace (e.g., knee brace, shoulder sling, sleeve, etc.). Thus, in one embodiment, the control unit can be used with and communicate with any number of goods, such as a sleeve, a wrap, a garment (e.g., shorts or compression shorts (CAM)), a brace, a sling, etc. The good can be for any body part, such as a knee, ankle, wrist, shoulder, back, calf, hip, thigh, elbow, etc. The good can be worn by the patient after surgery, during exercise, for arthritis, or any other time. The good can be rigid or flexible and can be worn, in one embodiment, across a joint.

In one embodiment, the control unit can connect with the soft good via a plug or port located on the good or connected to the good. Once connected, the control unit can, in one embodiment, read the program(s) to execute for the specific good and then can execute the program via communication with the sensors on the good. Thus, a single control unit can be used with any soft good(s) purchased or utilized by a patient. In one embodiment, the control unit can communicate (e.g., wirelessly) with the medical professional (e.g., doctor) periodically, at set times, when the program(s) are executed, or any other time or times. In one embodiment, the control unit is a physical device (e.g., that the patient can clip onto their belt or, e.g., in a pocket in the good). In another embodiment, the control unit is an "app" residing on a smartphone or computing device. In one embodiment, the control unit can download data to a computing device for review and/or analysis. In one embodiment, the control unit has a display that can display options to the user (e.g., medical professional or patient), such as to select the body part being supported, to select the program (e.g., waveform (s)) to execute, etc. In one embodiment, the control unit can be used to update the information stored on the soft good, such as by downloading new programs into the soft good for storage and future execution.

Figure 8:
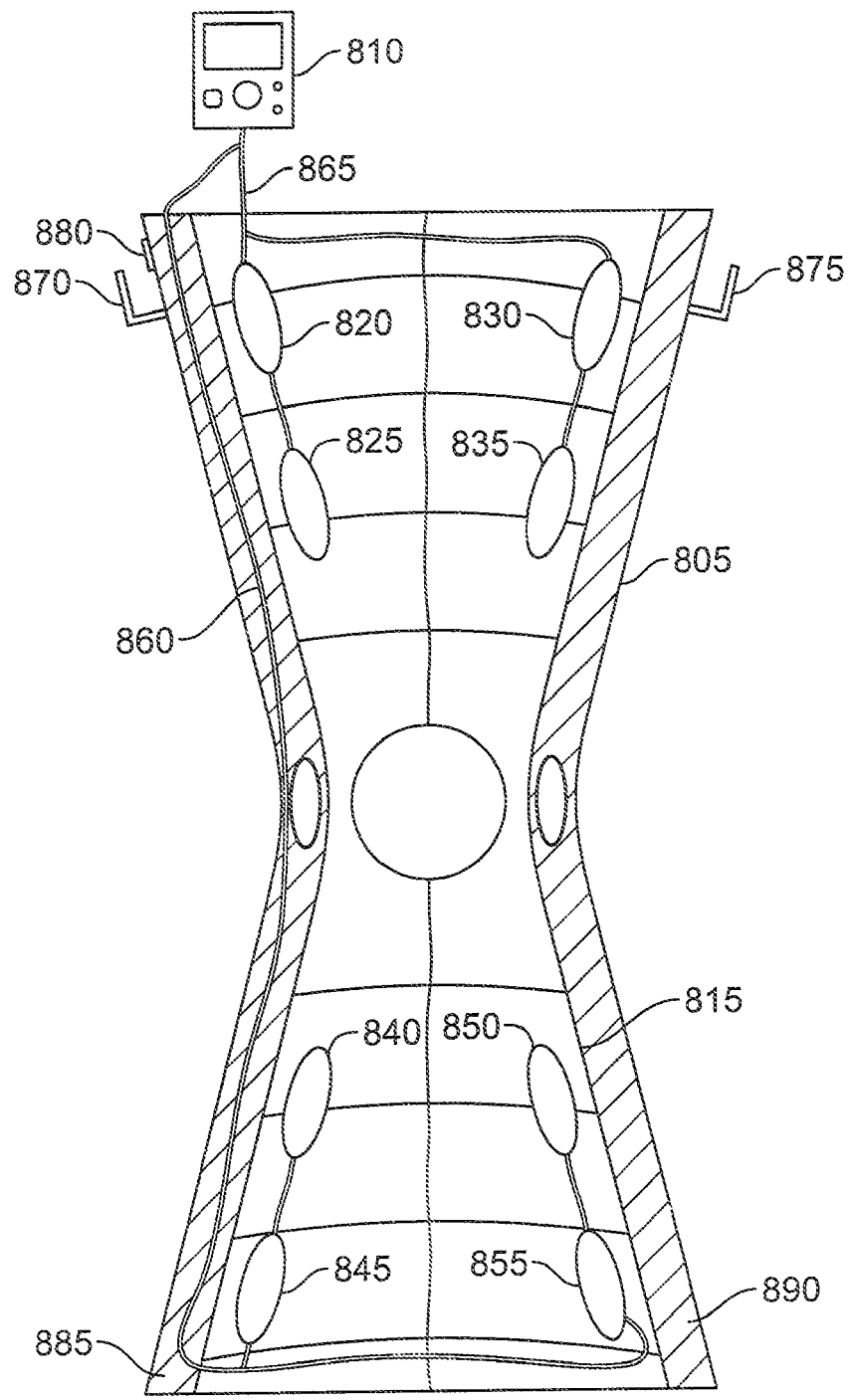
FIG. 8 is a perspective view of a soft good connected to a control unit in accordance with an embodiment of the disclosure.

FIG. 8 is a perspective view of an embodiment of a good 805 connected to control unit 810. In one embodiment, good 805 is a "short brace" that includes a sleeve/wrap 815 that is part of the good 805. In one embodiment, the sleeve/wrap 815 cannot be separated from the good 805. The sleeve/wrap 815 includes a number of sensors, such as a first upper sensor pair 820, 825 and a second upper sensor pair 830, 835, and a first lower sensor pair 840, 845 and a second lower sensor pair 850, 855. In one embodiment, the current flows between two connected sensors of a sensor pair, such as between sensor 820 and sensor 825. The connected sensor pairs form a channel. When one channel (e.g., between sensor 820 and sensor 825) is conducting current, the other channels (e.g., channel between sensors 830, 835) are floating and therefore no current is flowing between these other "floating" channels.

In one embodiment and as described in more detail below, photosets are used for high frequency isolation. Photofets facilitate noise isolation because there is an absorption band that minimizes high frequency noise for transitions between, for example, 0.01 and 0.1 milliseconds. Anything above that frequency (above 10 kHz) is removed, and because the transistors (FETS) are operated well beyond linear transition states, the drive signals are clean with little slew and no backscatter exhibited on output electrodes. Thus, photoisolation is used.

The sensors 820, 825, 830, 835, 840, 845, 850, 855 are connected to the control unit 810 via wires 860, 865. In another embodiment, the sensors 820, 825, 830, 835, 840, 845, 850, 855 are in communication with the control unit wirelessly. In one embodiment, the good 805 includes brackets 870, 875 for secure placement of the control unit 810. In one embodiment, the control unit 810 plugs into the good 805 via port 880. The good 805 includes stays 885, 890.

Figure 9:
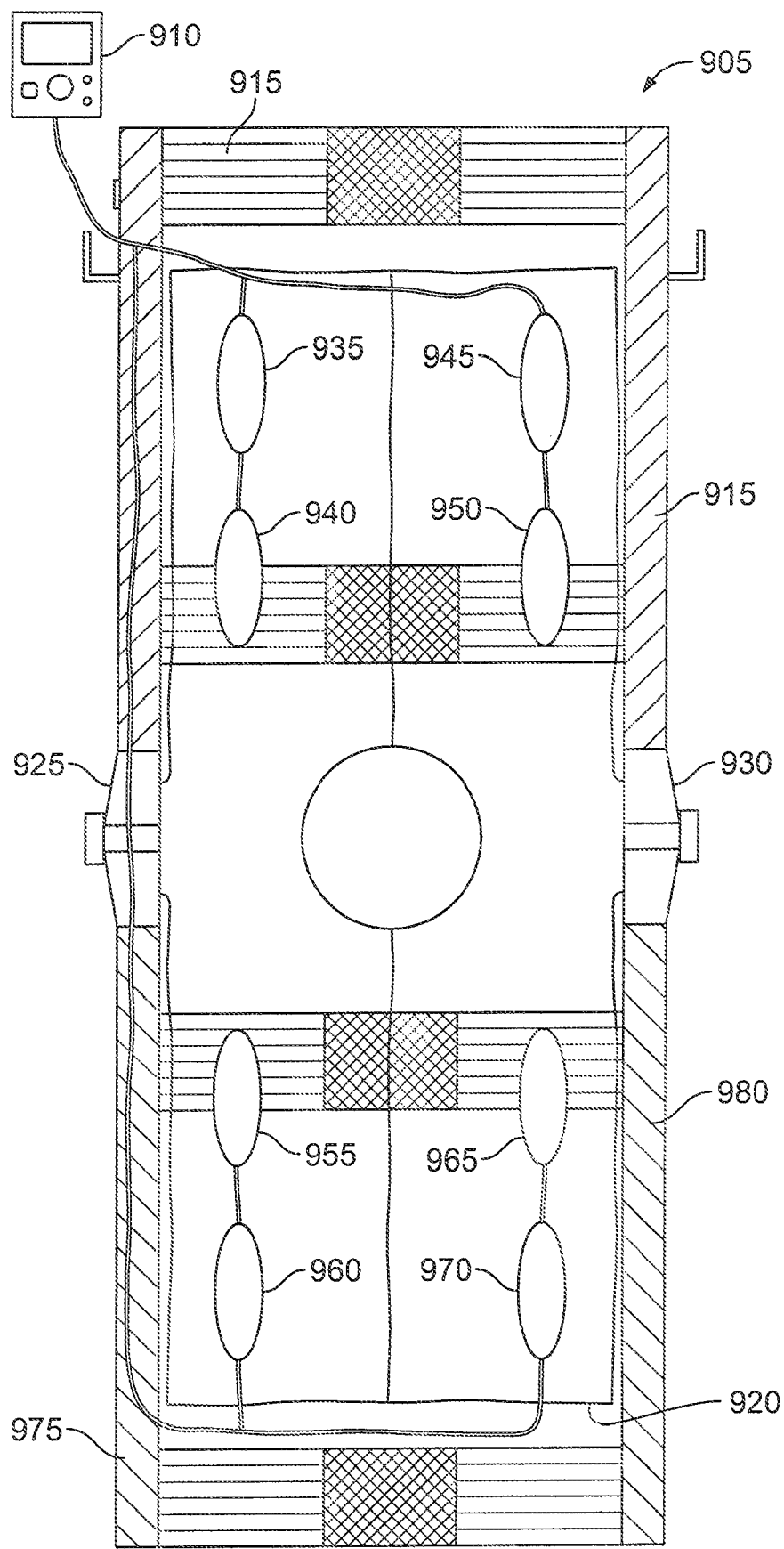
FIG. 9 is a perspective view of a soft good connected to a control unit in accordance with an embodiment of the disclosure.

FIG. 9 is a perspective view of an embodiment of a good 905 connected to control unit 910. In one embodiment, good 905 is a "long brace" that includes a brace 915 and a sleeve/wrap 920 that is inside the brace 915. In one embodiment, the sleeve/wrap 920 is connected to the brace 915 at hinges 925, 930. The hinges 925, 930 can be adjustable hinges, such as hinges that can adjust between 0°, 45°, 90°, and open. In one embodiment, the sleeve/wrap 920 can be separated from the brace 915. The sleeve/wrap 920 includes a number of sensors, such as a first upper sensor pair 935, 940 and a second upper sensor pair 945, 950, and a first lower sensor pair 955, 960 and a second lower sensor pair 965, 970. As described above, in one embodiment the current flows between two connected sensors of a sensor pair, such as between sensor 935 and sensor 940. The connected sensor pairs form a channel. When one channel (e.g., between sensor 935 and sensor 940) is conducting current, the other channels (e.g., channel between sensors 945, 950) are floating and therefore no current is flowing between these other "floating" channels. The brace 915 includes stays 975, 980.

In one embodiment, the long brace 905 is a brace 915 with sleeve/wrap 920 that extends past the joint (e.g., knee). Thus, unlike the short brace 805, which has an attached sleeve 815, the long brace 905 has a sleeve 920 that enables removal of the brace 915 from the sleeve 920.

In one embodiment, each sensor is packaged with moisturizer (e.g., a generic hand cream) applied thereon. Each sensor with moisturizer can have, for instance, a cellophane cover on the sensor and the patient or medical professional would remove the cellophane cover when the good is removed from its package. In one embodiment, the sensor will sense how dry the patient's skin is and communicate this information to the control unit. The control unit can then provide a notification to the patient or medical professional that the patient's skin needs to be moisturized.

In one embodiment, the sleeve, brace, or good provides support to the calf muscle of a patient and electrodes/sensors apply EMS to the calf muscle in a closed loop fashion as described. Thus, in one embodiment, the soft good stimulates the calf muscle(s) to facilitate prevention of deep vein thrombosis (DVT).

In one embodiment, the good can be a garment providing lumbar support. The garment can cross the hip joint and can have electrodes on one or both sides of the hip joint while also providing back support. In one embodiment, the electrodes are placed around one or more of the hip, the lower back, and the legs.

Calf stimulation and quad stimulation typically require application of EMS with different amplitudes. Thus, the closed loop system can be used to monitor amplitude. One sleeve can do different muscle groups and because monitoring reaction of muscle to stimulation and adjusting amplitude of pulse via the described closed loop system, one good (e.g., sleeve) can be used in one embodiment for different muscle groups.

In more detail, in one embodiment the power dissipation of a short "sense pulse" is obtained before each stimulation pulse. Each stimulation pulse is adjusted based on one or more power dissipation measurements in order to maintain constant power output across each pulse. Each electrode used to provide the electrical stimulation contains a sensor so that the power dissipation is determined at the stimulation site.

The closed loop provides several benefits. For example, if the measured power dissipation from the sensing pulse exceeds preset boundaries, the device will end its stimulation sequence before discharging the stimulation pulse. As another benefit, each sense pulse creates or maintains a conductive channel through the human tissues by exceeding the breakdown voltage of the human tissues. The creation of this dielectric breakdown improves efficiency and safety by reducing the power required to contract a desired muscle with a given stimulation pulse. By reducing the power requirements of the stimulation pulses and maintaining constant power across every stimulation pulse, the risk of painful shocks and skin burns is eliminated. Further, the overall efficiency of the unit is dramatically improved, allowing for a reduction in size of the electrical components compared to existing units, making the brace more portable and easier to use.

One advantage of applying constant power is avoiding the harmful effects of cellular damage. A cell has a maximum wattage it can survive. After overcoming the dielectric constant, conventional units may introduce cellular damage. Once the dielectric constant is overcome, milliWatts of power are needed. Thus, once the dielectric breakdown occurs and current is flowing, the control electronics 210 reduces the power to a fixed, low power that in one embodiment can be adjusted by the user.

Once power dissipation is determined, the power to pump into the human tissues can be determined after the conductive channel is created. The channel is maintained, and can determine characteristics of the channel (e.g., power received and power transmitted). Thus, power dissipation can be determined.

The device self tunes it's electrical output by modifying the drive voltage of the HV power supply in order to maintain the desired output power (e.g., in watts). The required power output is calculated by measuring the power dissipation of the electrical circuit formed by the electrodes and the human tissues and applying one or more algorithms to the power dissipation measurement and the desired waveform data.

In order to achieve this, the output of a flyback mode switching power supply is modified to generate a stable, regulated DC. By taking this approach rather than the traditional approach of a push-pull driver against a transformer, we can provide a clean DC signal, rather than a noisy signal with potential high frequency A/C. This is essential for accurate measurement, and true closed loop operation.

Figure 10A:
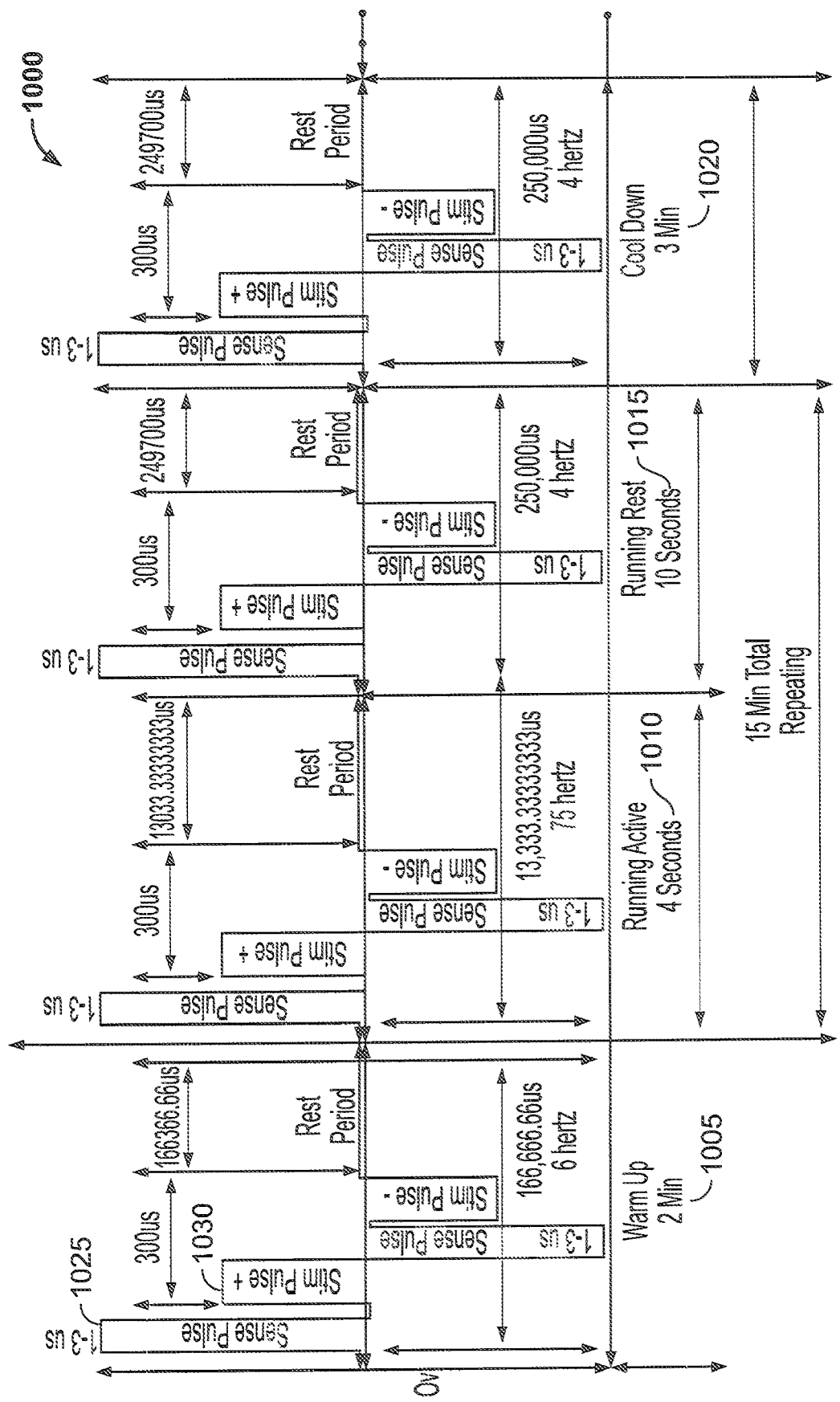
FIG. 10A is a signal diagram illustrating the signals transmitted into the human tissues by the electrodes/sensors in accordance with an embodiment of the disclosure.

In one embodiment, the power dissipation is measured before every stimulation pulse and the stimulation pulse is adjusted to maintain a constant power output for each pulse. Referring now to FIG. 10A, the DC signals 1000 transmitted into the human tissues by the electrodes/sensors are shown. The signals 1000 include a warm up phase 1005, a running active phase 1010, a running rest phase 1015, and a cool down phase 1020. Each phase includes a sense pulse (referred to hereinafter as sense pulse 1025), which is a short pulse to overcome the dielectric constant of the human tissues (to create an ion channel in the human tissues so that current can flow), and to sense the power loss in the circuit to determine how much power in a stimulation pulse should be applied (and to determine whether it is safe to transmit the stimulation pulse, as described in more detail below). The sense pulse 1025 in one embodiment is approximately 10-180 V and lasts 1-3 μs. After the sense pulse is transmitted, the sensor typically transmits a stimulation pulse (hereinafter stimulation pulse 1030). The stimulation pulse 1030 is, in one embodiment, approximately 18-20V and typically in the range of 1 μs to 200 μs. Thus, after the sense pulse 1025, the voltage drops significantly to limit the current. Then the power dissipation is measured before the introduction of the next stimulation pulse 1030. In one embodiment, the power transmitted is dissipated before the change in polarity of the signals, thereby preventing charge transfer during zero crossing, ensuring the signal remains purely DC.

In one embodiment, there is a gap in time between the end of the sense pulse 1025 and the start of the stimulation pulse 1030. The pulses then switch polarity. Thus, before every stimulation pulse 1030, the sensor transmits a sense pulse 1025 to determine how much power has been dissipated and whether it is safe to deliver the stimulation pulse 1030. The signals produced after the sense pulse introduce a very small power factor, on the order of milliWatts.

Figure 10B:
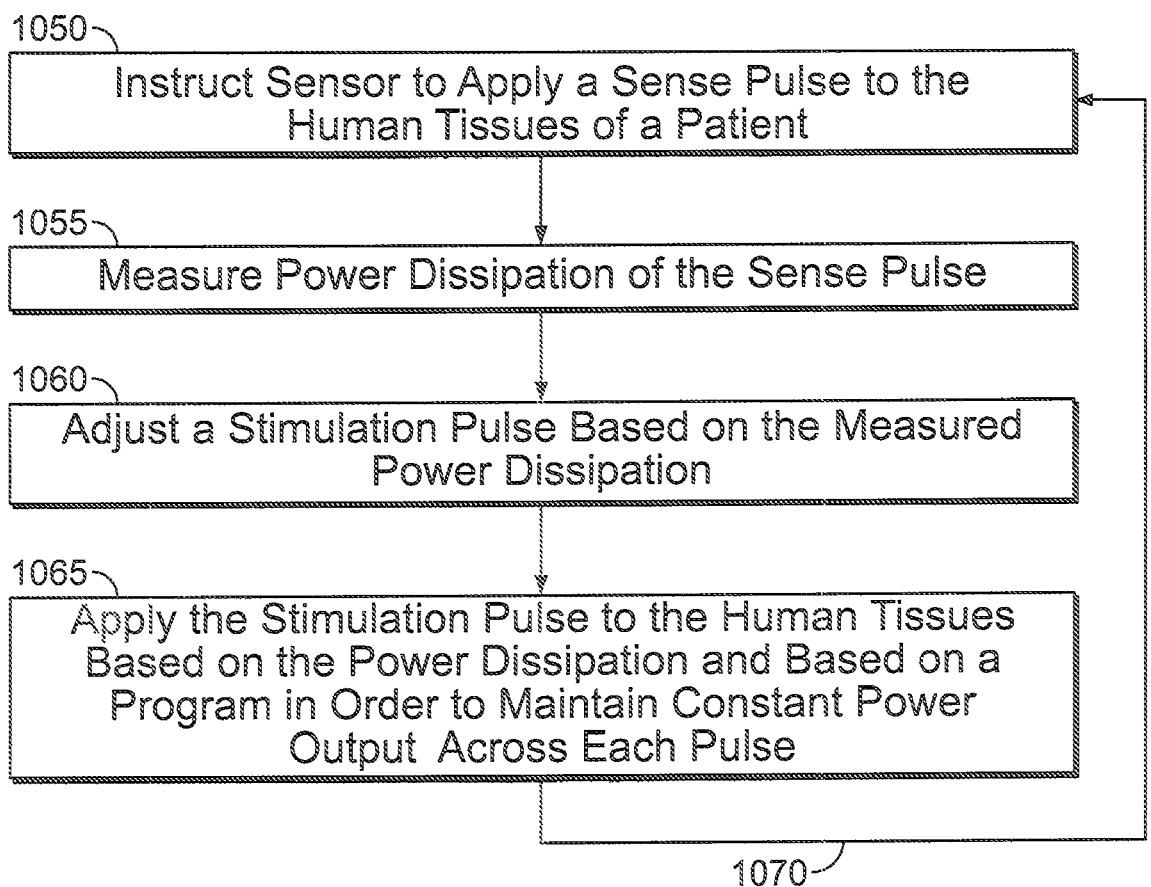
FIG. 10B is a flowchart showing steps performed by the control electronics in accordance with an embodiment of the disclosure.

FIG. 10B is a flowchart showing an embodiment of steps performed by the control electronics. The control electronics instructs a sensor in a sensor pair to apply the sense pulse 1025 to the human tissues of a patient (Step 1050). The sensor (or other sensor in the sensor pair) measures the power dissipation of the sense pulse 1025 in the human tissues (Step 1055). The control electronics adjusts the stimulation pulse 1030 based on the measured power dissipation (Step 1060). The control electronics then instructs the sensor to apply the stimulation pulse 1030 to the human tissues based on the power dissipation and based on the program in the good in order to maintain constant power output across each pulse. Steps 1050-1065 are repeated (Step 1070).

Figure 11:
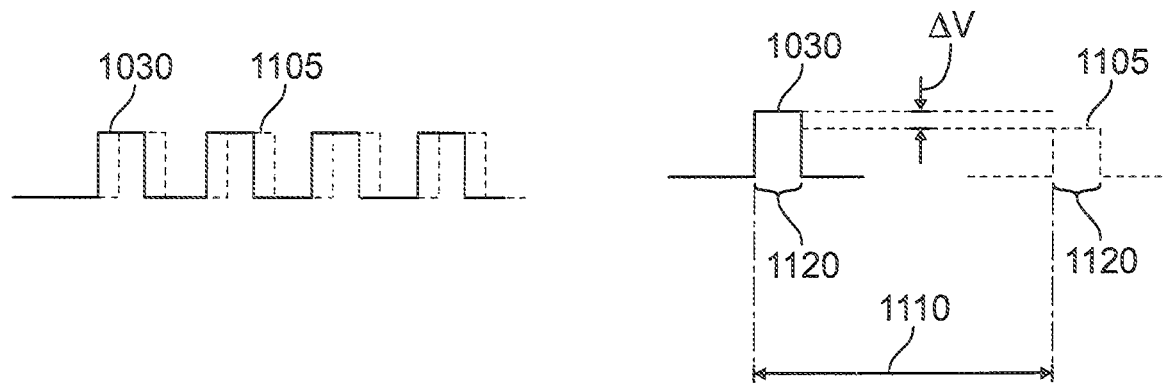
FIG. 11 is a signal diagram illustrating the propagation delay between the stimulation pulse and the receive pulse transmitted and received by the electrodes/sensors in accordance with an embodiment of the disclosure.

Referring to FIG. 11, the other sensor in the pair of sensors (per sensor channel) provides the return path for the electrical current from the transmission of the stimulation pulses 1030. In one embodiment, the sense pulse 1025 measures how long it takes to receive a return pulse 1105 on the receiving electrode side. If the sensor determines the propagation delay between sent pulse (e.g., pulse 1025) and return pulse 1105, the sensor (or control electronics 210) can determine the maximum stimulation pulse 1030 to apply. The return pulse 1105 is typically a square pulse.

As shown in FIG. 11, the propagation delay 1110 between the stimulation pulse 1030 and the receive pulse 1105 is the time difference between the start time of the stimulation pulse 1030 and the start time of the receive pulse 1105. The change in distortion 1120 is the difference between the pulse widths of the two pulses 1030, 1105. In one embodiment, the change in distortion is used to determine whether the muscle is being charged as an inductor and whether the muscle is storing power. In one embodiment, the change in distortion is for calibrating the algorithm and another point of feedback. In one embodiment, the gel applied with the sensors (e.g., hydrogel) is introducing (or increasing) the propagation delay.

Figure 12:
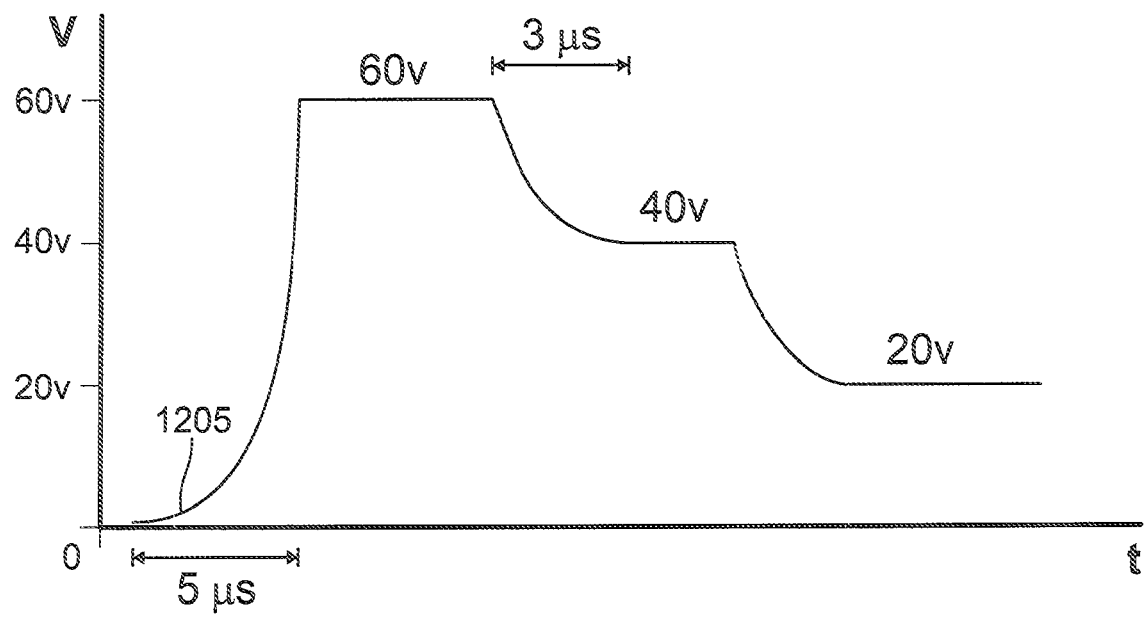
FIG. 12 is a signal diagram illustrating the power supply signal produced by the power supply in accordance with an embodiment of the disclosure.

FIG. 12 shows an embodiment of a power supply signal 1200 produced by the power supply (as described in more detail below). The power supply signal 1200 includes a ramp up phase 1205 that typically lasts 5 μs. In one embodiment, the voltage peaks at 60 V, and then drops down after a period of time to 40V. In one embodiment, the voltage signal then drops down, after a second period of time, to 20 V. The power supply can be a voltage controlled power supply or a current controlled power supply. When an increase in current (or voltage) is needed, the power is increased.

The conventional power supplies used with electrical stimulation for braces or wearable components typically utilize multiple pulses (power generation and switching technology). They often generate a 24 V supply and then have a transformer, H-bridge, and produce a pulse train (with a ripple), where the transformer averages the signal out (e.g., 1:10 or 1:20 ratio). Unlike these conventional systems, the power supply here provides a steady signal with a small ramp up phase, which enables the closed loop system.

Our output is an analog voltage upon which current is clamped. This power supply enables precise and accurate, virtually noise-free measurements. The conventional power supplies induce current flow based on pulse-width modulation (PWM). PWM systems do not enable precise and accurate measurements due to the noise introduced from PWM and due to field saturation of their transformer(s). Further, the power supply in this system enables a wide range of waveforms and protocols to be run based on the information stored on the soft good. Additionally, if it is determined that a protocol is harmful and cannot be run (e.g., determined by the FDA), this power supply enables the system to be operational much faster than others because only the soft good needs to be changed.

In one embodiment, 0-3.3 V input voltage controls the output across the full targeted range of the power supply. Thus, to generate the 60 V output maximum range, 3.3 V is provided as reference input to the power supply. In one embodiment, a dedicated voltage controlled power supply is present per channel, which means there is no time division. Conventional power supplies use time division to supply power to multiple electrodes. Here, there is no time division.

Figure 13:
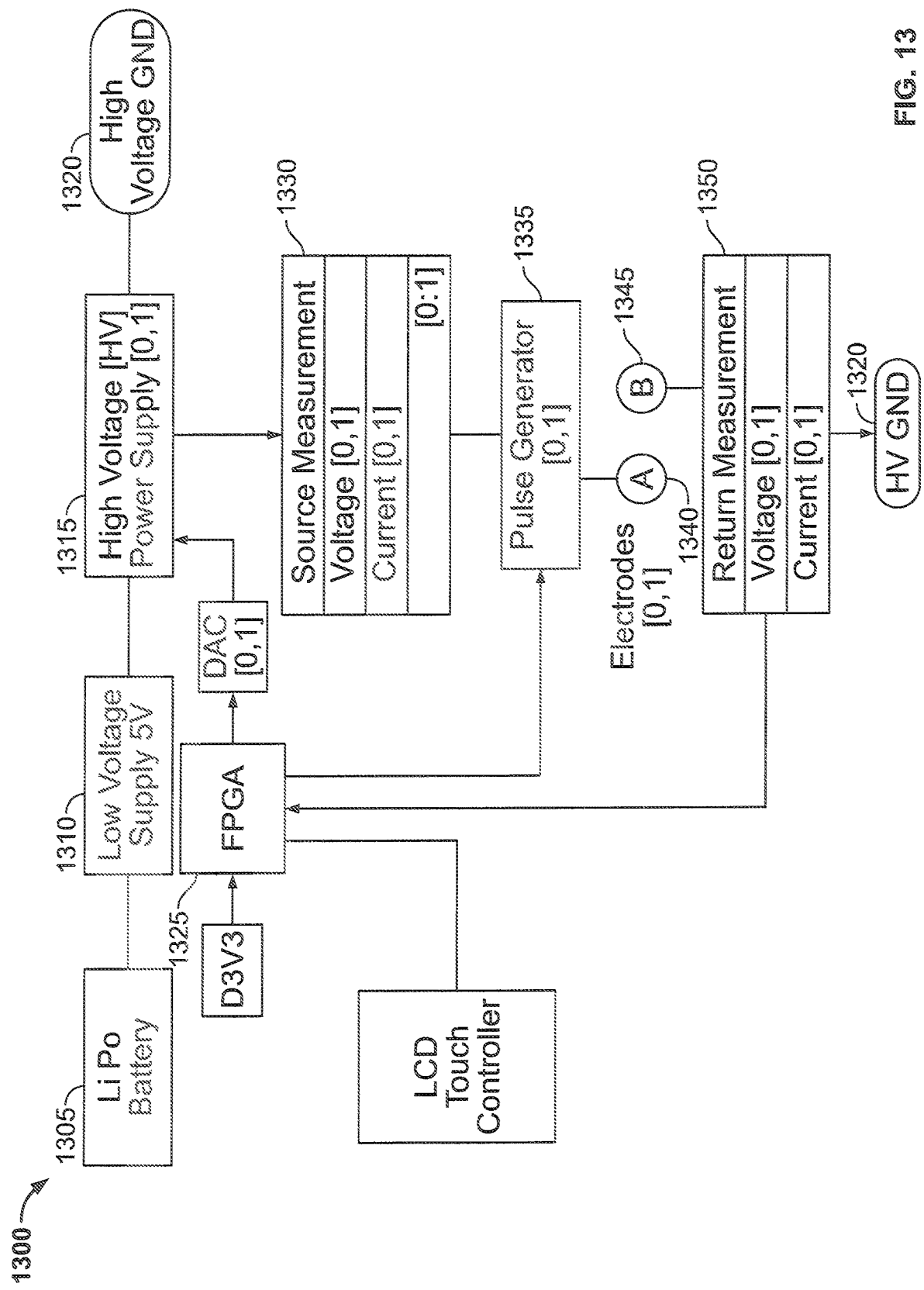
FIG. 13 is a block diagram of a circuit that can measure the dynamic properties of the electrodes in a channel in accordance with an embodiment of the disclosure.

FIG. 13 is a block diagram of an embodiment of a circuit 1300 that can measure the dynamic properties of the electrodes in a channel, such as current, voltage, resistance, capacitance, and/or inductance. A battery 1305 connects to a low voltage power supply 1310 (e.g., 5 V, which supplies the 3.3 V identified above), which connects to a high voltage (HV) power supply 1315. The HV power supply 1315 connects to ground 1320. The HV power supply 1315 provides the sense pulse 1025. In one embodiment, the HV power supply 1315 also provides the stimulation pulse 1030. A field-programmable gate array (FPGA) 1325 connects to a digital-to-analog converter (DAC), which connects to the HV power supply 1315. The FPGA 1325 is a massively parallel microcontroller computer-a programmable analog chip with a program burned onto it. The FPGA 1325 is based on a clock and is completely analog. Thus, there is no time division or multiplexing. Although described as a FPGA, any programmable logic device (PLD) can be used. The FPGA 1325 also connects to a digital power supply D3V3.

The HV power supply 1315 can obtain source measurements (e.g., voltage or current), as shown in block 1330. In one embodiment, source measurement block 1330 is a source measurement circuit. A pulse generator 1335 connects to electrode A 1340 (the transmitting electrode/sensor in this instance). The pulse generator 1335 is connected to the FPGA 1325.

Electrode B 1345, the return electrode/sensor representing the output, connects to a return measurement block (or circuit) 1350, which also connects to the FPGA 1325 and HV ground 1320. In one embodiment, the return measurement block/circuit 1350 is identical to the source measurement block/circuit 1330. In one embodiment, the FPGA 1325 also connects to an LCD touch controller for controlling the circuit 1300.

Figure 14:
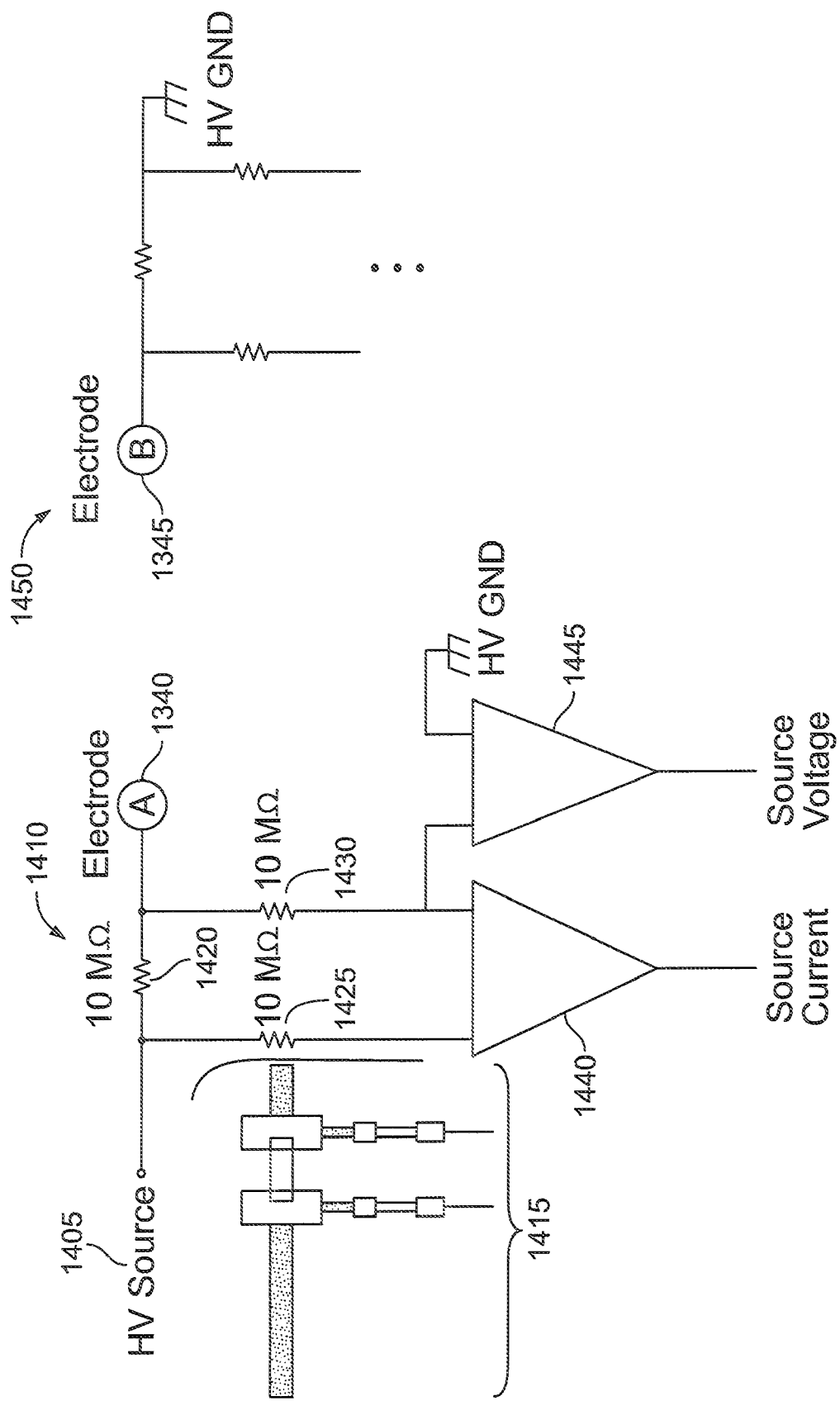
FIG. 14 is an analog sense circuit to measure the source voltage and source current in accordance with an embodiment of the disclosure.

Referring to FIG. 14, the analog sense circuit to measure the source voltage and source current is shown. An HV source 1405 is applied to a resistor network 1410 connected to a shunt 1415. In one embodiment, a first resistor 1420 is a 10Ω 0.1% resistor and is connected to a second and third resistor 1425, 1430 that are, in one embodiment, 1 MΩ 0.01% resistors. The resistor network 1410 is connected to the electrode A 1340. The shunt 1415 is connected to a wide trace in and wide trace out for power with a pull-up tap. The resistors 1425, 1430 are connected to a first operational amplifier (op-amp) 1440 to measure source current. Resistor 1430 is connected to a second op-amp 1445 to measure source voltage. The other side of the circuit (circuit 1450) is connected to electrode B 1345 and is the same circuit as the circuit with resistor network 1410, shunt 1415, and op-amps 1440 and 1445. Thus, these circuits enable measurement of input power and output power. Although the resistors 1420, 1425, 1430 are shown with particular values, these values are arbitrary and any corresponding resistor values can be used.

Figure 15:
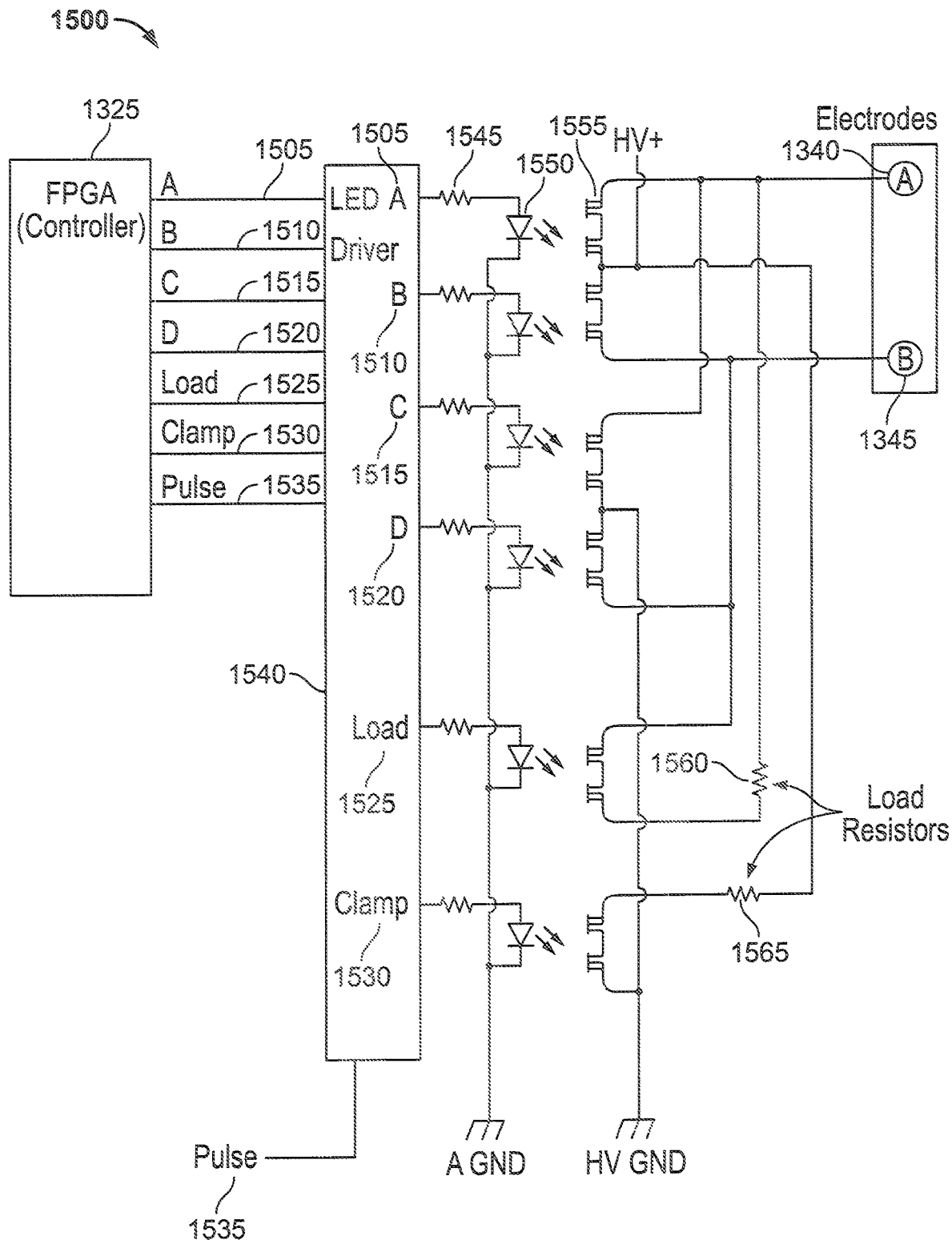
FIG. 15 is a circuit diagram of a circuit to generate a stimulation pulse in accordance with an embodiment of the disclosure.

FIG. 15 is an embodiment of a circuit 1500 to generate a stimulation pulse 1030. The circuit 1500 uses optically coupled FETs (also referred to as solid state relays (SSRs) or optoFETs) to generate the stimulation pulse 1030 because of a low electromagnetic interference (EMI) waveform generated by the circuit 1500. This prevents interference with precision instruments and medical equipment so that this circuit (and, therefore, a brace utilizing this circuit) can be used in the operating room or near sensitive medical equipment.

As stated above, in one embodiment, the circuit 1500 includes a controller, which can be an FPGA 1325. The controller 1325 includes an A output 1505, a B output 1510, a C output 1515, a D output 1520, a LOAD output 1525, a CLAMP output 1530, and a PULSE output 1535. These outputs are optionally provided to an LED driver 1540. Each output of the LED driver is connected to an LED resistor (hereinafter LED resistor 1545) and an LED (hereinafter LED 1550). The LED 1550 is optically coupled to the SSR (hereinafter SSR 1555). As shown in circuit 1500, different SSRs 1555 are connected to electrode(s) 1340, 1345. The circuit 1500 also includes two load resistors 1560, 1565.

The LEDs 1550 turn power on and off in the circuit 1500, and in one embodiment the LEDs 1550 and SSRs 1555 are in a shielded light proof box (or encased in an integrated circuit) to electrically isolate those components of the circuit 1500. The SSRs 1555 work on a voltage differential, and there is no reference from gate voltage to source or drain. In one embodiment, one SSR chip includes two SSRs and the corresponding LEDs.

Clamp 1530 is to clamp the power supply, so that when the voltage from the power supply needs to drop quickly, the clamp activates. The clamp has to be released in order to drive the circuit 1500. Thus, when the clamp 1530 and load resistors 1560, 1565 are engaged, the load is applied across the electrodes 1340, 1345 and if the system experiences a failure or an out of range value, the circuit 1500 will fail safe and nothing harmful will happen to the patient. This safety feature enables the brace to be worn at all times, without worrying about where the patient is located (e.g., driver or passenger of automobile, in a swimming pool, etc.). The circuit 1500 will not just turn on or send a stimulation pulse without adequate and proper activation. If there is a short circuit, the circuit 1500 applies a load across the electrodes 1340, 1345. If the patient fell into a pool wearing a device utilizing circuit 1500, the device would fail safe. In other words, the patient would not be harmed if this occurred (or if any out of range input was provided to one or both of the electrodes 1340, 1345). Thus, unlike conventional systems, which often require the user to increase the power being input to the muscles or human tissues after a certain amount of time, this system recognizes an out of bounds signal and often results in a decrease in resistance (as you activate muscle, ion channel through muscle increases) and power due to power dissipation after the initial sense pulse. Thus, the system minimizes pain experienced by the patient because of the closed loop nature of the system and the decision-making process that occurs after each pulse.

When a signal is applied, the SSRs 1555 close and complete the circuit. The load resistors are typically closed and only open when the system powers up. The LED resistors 1545 are typically open. The circuit 1500 doesn't allow a high voltage supply to come up to a high voltage because the load resistors 1560, 1565 are held across it and force the high voltage supply to shut down. This removes many single points of failure. The high voltage power supply can also sense overcurrent.

When CLAMP 1530 is high (active), this removes the load resistor 1565 from the circuit. When LOAD 1525 is high (active), it removes the load resistor 1560 from the circuit. Thus, the LOAD 1525 applies load resistor 1560 across the electrodes 1340, 1345. CLAMP 1530 clamps them to a high voltage power supply. This setup can help with calibration. In one embodiment, the load resistors 1560, 1565 are 10Ω power resistors.

The optional LED driver 1540 is a digital buffer that sources current I to drive the LEDs 1550. PULSE 1535 is active low. The LED driver 1540 polls the PULSE signal 1535 and then sets the direction bits. To generate a stimulation pulse 1030, one way is to have A 1505 high (high voltage to electrode A 1340) and D 1520 high. This will cause current to flow in one direction (e.g., from electrode A 1340 to electrode B 1345). If C 1515 is high and B 1510 is high, current flows the other way (e.g., from electrode B 1345 to electrode A 1340).

FIG. 16 is an embodiment of the input waveform 1605, a desired output waveform 1610, and a target voltage 1615. The dashed lines are reference lines. The input waveform 1605 is the same waveform as shown in FIG. 10A (with the sense pulse 1025 and the stimulation pulse 1030). The desired output waveform 1610 includes a pulse for each sense and stimulation pulses 1025, 1030. The target voltage 1615 is a voltage for the 0-3.3. V/5 V reference voltage as identified above. This is different than a typical PWM signal in that it is a pure analog signal.

Those skilled in the art will recognize that the methods and systems of the present disclosure may be implemented in many manners and as such are not to be limited by the foregoing exemplary embodiments and examples. In other words, functional elements being performed by single or multiple components, in various combinations of hardware and software or firmware, and individual functions, may be distributed among software applications at either the user computing device or server or both. In this regard, any number of the features of the different embodiments described herein may be combined into single or multiple embodiments, and alternate embodiments having fewer than, or more than, all of the features described herein are possible. Functionality may also be, in whole or in part, distributed among multiple components, in manners now known or to become known. Thus, myriad software/hardware/firmware combinations are possible in achieving the functions, features, interfaces and preferences described herein. Moreover, the scope of the present disclosure covers conventionally known manners for carrying out the described features and functions and interfaces, as well as those variations and modifications that may be made to the hardware or software or firmware components described herein as would be understood by those skilled in the art now and hereafter.

While the system and method have been described in terms of one or more embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

What is claimed is:

1. A system for delivering electrical stimulation comprising:
    a first set of electrodes,
    a first channel,
    a first voltage supply,
    a second set of electrodes,
    a second channel,
    a second voltage supply, and
    a controller;
    wherein the first set of electrodes comprises the first channel;
    wherein the second set of electrodes comprises the second channel;
    wherein the first channel comprises the first voltage supply;
    wherein the second channel comprises the second voltage supply;
    wherein the first voltage supply is configured to supply a first stimulation pulse;
    wherein the second voltage supply is configured to supply a second stimulation pulse;
    wherein the controller is programed to transmit the first stimulation pulse and the second stimulation pulse at different voltages to a respective first stimulation site and second stimulation site;
    wherein the controller is programed to transmit the first stimulation pulse and the second stimulation pulse within the same time domain;
    wherein the controller is programed to receive power dissipation information from a sense pulse from each of the first set of electrodes and the second set of electrodes at a respective stimulation site; and
    wherein the system is configured and arranged to result in co-coupled contraction of different muscle groups.

2. The system of claim 1,
    wherein each electrode of the first set of electrodes and second set of electrodes comprise a sensor; and
    where each sensor and each electrode share a common contact point.

3. The system of claim 1,
    wherein the controller is programmed to execute a power dissipation measurement of the power dissipation of the sense pulse before each respective stimulation pulse.

4. The system of claim 3,
    wherein the controller is programmed to execute each sense pulse for a shorter time duration than each respective stimulation pulse.

5. The system of claim 3,
    wherein the controller is programmed to change a polarity between each sense pulse and each respective stimulation pulse.

6. The system of claim 3,
    wherein the controller is programmed to implement a gap in a time between an end of the sense pulse and a start of the stimulation pulse.

7. The system of claim 1,
    wherein the controller is programmed to execute an adjustment to a respective stimulation pulse based on the power dissipation measurement of the sense pulse to maintain a constant power output for each respective stimulation pulse.

8. The system of claim 7,
    wherein the controller is programmed to execute each sense pulse at a higher voltage than each respective stimulation pulse.

* * * * *